US012673074B2

(12) United States Patent
Kampinga et al.

(10) Patent No.: US 12,673,074 B2
(45) Date of Patent: Jul. 7, 2026

(54) MYCOBACTERIUM FOR USE IN CANCER THERAPY

(71) Applicant: TONRON INTERNATIONAL LIMITED, Airdrie (GB)

(72) Inventors: Jakob Kampinga, Groningen (NL); Thomas Kleen, Uxbridge (GB)

(73) Assignee: TONRON INTERNATIONAL LIMITED, Airdrie (GB)

( * ) Notice: Subject to any disclaimer, the term of this patent is extended or adjusted under 35 U.S.C. 154(b) by 315 days.

(21) Appl. No.: 18/252,206

(22) PCT Filed: Nov. 10, 2021

(86) PCT No.: PCT/GB2021/052905
§ 371 (c)(1),
(2) Date: May 9, 2023

(87) PCT Pub. No.: WO2022/101619
PCT Pub. Date: May 19, 2022

(65) Prior Publication Data
US 2023/0405059 A1 Dec. 21, 2023

(30) Foreign Application Priority Data

Nov. 10, 2020 (GB) ..................................... 2017752
Mar. 29, 2021 (GB) ..................................... 2104431

(51) Int. Cl.
| A61K 35/74 | (2015.01) |
| A61K 9/00 | (2006.01) |
| A61K 31/337 | (2006.01) |
| A61K 31/7068 | (2006.01) |
| A61K 45/06 | (2006.01) |
| A61P 35/00 | (2006.01) |

(52) U.S. Cl.
CPC ............ *A61K 35/74* (2013.01); *A61K 9/0021* (2013.01); *A61K 31/337* (2013.01); *A61K 31/7068* (2013.01); *A61K 45/06* (2013.01); *A61P 35/00* (2018.01)

(58) Field of Classification Search
None
See application file for complete search history.

(56) References Cited

U.S. PATENT DOCUMENTS

| 8,617,520 B2 | 12/2013 | Akle et al. |
| 10,610,577 B2 | 4/2020 | Akle et al. |
| 10,610,578 B2 | 4/2020 | Akle et al. |
| 10,925,952 B2 | 2/2021 | Akle et al. |
| 10,994,002 B2 | 5/2021 | Akle et al. |
| 11,000,584 B2 | 5/2021 | Akle et al. |
| 11,207,405 B2 | 12/2021 | Akle et al. |
| 11,318,193 B2 | 5/2022 | Akle et al. |
| 11,554,166 B2 | 1/2023 | Akle et al. |
| 2021/0213127 A1 | 7/2021 | Akle et al. |
| 2021/0213128 A1 | 7/2021 | Akle et al. |
| 2021/0299187 A1 | 9/2021 | Martyn et al. |
| 2022/0111046 A1 | 4/2022 | Akle et al. |
| 2023/0050258 A1 | 2/2023 | Martyn |
| 2023/0084300 A1 | 3/2023 | Martyn et al. |
| 2023/0405114 A1 | 12/2023 | Martyn et al. |

FOREIGN PATENT DOCUMENTS

WO WO 2020/002905 1/2020

OTHER PUBLICATIONS

International Search Report and Written Opinion in International Application No. PCT/GB2021/052905, Feb. 18, 2022, pp. 1-16.
Claims as filed for U.S. Appl. No. 18/154,177, filed Jan. 18, 2023, pp. 1-3.
Costa Neves, M. et al. "Extended Survival after Complete Pathological Response in Metastatic Pancreatic Ductal Adenocarcinoma Following Induction Chemotherapy, Chemoradiotherapy, and a Novel Immunotherapy Agent, IMM-101" *Cureus*, published Dec. 26, 2015, pp. 1-8, vol. 7, No. 12.
Dalgleish, A. G. et al. "Randomised, open-label, phase II study of gemcitabine with and without IMM-101 for advanced pancreatic cancer" *British Journal of Cancer*, published online Sep. 6, 2016, pp. 789-796, vol. 115, No. 7.
Mendes, R. et al. "Clincal and immunological assessment of *Mycobacterium vaccae* (SRL172) with chemotherapy in patients with malignant mesothelioma" *British Journal of Cancer*, 2002, pp. 336-341, vol. 86, No. 3.
Vivaldi, C. et al. "First-line gemcitabine plus nab-paclitaxel for elderly patients with metastatic pancreatic cancer: Crossing the frontier of age?" *European Journal of Cancer*, available online Aug. 1, 2020, pp. 108-116, vol. 137.

*Primary Examiner* — Brian Gangle
(74) *Attorney, Agent, or Firm* — SALIWANCHIK, LLOYD & EISENSCHENK

(57) ABSTRACT

This invention provides an immunomodulator for use in the treatment, reduction, inhibition or control of cancer subject, wherein the subject is clinically classified as having a performance status of 1-, 2, 3 or 4 according to the ECOG Scale, or classified as not being of an age and/or not being sufficiently fit to tolerate two or more chemotherapy regimens. The invention also describes the use of one or more additional anticancer treatments or agents as well as protocols and dosage regimens for use.

20 Claims, 4 Drawing Sheets

MYCOBACTERIUM FOR USE IN CANCER THERAPY

CROSS-REFERENCE TO RELATED APPLICATION

This application is the U.S. national stage application of International Patent Application No. PCT/GB2021/052905, filed Nov. 10, 2021.

FIELD OF THE INVENTION

The present invention relates to the field of cancer therapy. In particular, the present invention relates to a method of preventing, treating or inhibiting the development of tumours and/or metastases in a subject using a *Mycobacterium* preparation.

BACKGROUND OF THE INVENTION

In humans with advanced cancer, anti-tumour immunity is often ineffective due to the tightly regulated interplay of pro- and anti-inflammatory, immune-stimulatory and immuno-suppressive signals. For example, loss of the anti-inflammatory signals leads to chronic inflammation and prolonged proliferative signalling. Interestingly, cytokines that both promote and suppress proliferation of the tumour cells are produced at the tumour site. It is the imbalance between the effects of these various processes that results in tumour promotion.

Pancreatic cancer is the third most common cause of cancer death. The mean life expectancy from diagnosis to death is approximately 6 to 12 months. Unfortunately, the low survival rate is due to the lack of symptoms in the early stages of cancer development. Therefore, by the time symptoms manifest, the pancreatic cancer has already started to metastasise making pancreatic cancer difficult to treat successfully.

To date, a major barrier to attempts to develop effective immunotherapy for cancers, such as pancreatic cancer, has been an inability to break immunosuppression at the cancer site and restore normal networks of immune reactivity. The physiological approach of immunotherapy is to normalize the immune reactivity so that, for example, the endogenous tumour antigens would be recognized and effective cytolytic responses would be developed against tumour cells. Although it was once unclear if tumour immunosurveillance existed, it is now believed that the immune system constantly monitors and eliminates newly transformed cells. Accordingly, cancer cells may alter their phenotype in response to immune pressure in order to escape attack (immunoediting) and upregulate expression of inhibitory signals. Through immunoediting and other subversive processes, primary tumours and metastasis maintain their own survival.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as checkpoint regulators. They act as molecular "tollbooths," which allow extracellular information to dictate whether cell cycle progression and other intracellular signalling processes should proceed. In addition to specific antigen recognition through the T-cell Receptor (TCR), T-cell activation is regulated through a balance of positive and negative signals provided by costimulatory receptors. These surface proteins are typically members of either the TNF receptor or B7 superfamilies. Agonistic antibodies directed against activating co-stimulatory molecules and blocking antibodies against negative costimulatory molecules may enhance T-cell stimulation to promote tumour destruction.

Two ligands specific for PD-1 have been identified: programmed death-ligand 1 (PD-L1), also known as B7-H1 or CD274) and PD-L2 (also known as B7-DC or CD273). PD-L1 and PD-L2 have been shown to down-regulate T cell activation upon binding to PD-1 in both mouse and human systems. The interaction of PD-1 with its ligands, PD-L1 and PD-L2, which are expressed on antigen-presenting cells (APCs) and dendritic cells (DCs), transmits negative regulatory stimuli to down-modulate the activated T cell immune response. Blockade of PD-1 suppresses this negative signal and amplifies T cell responses.

The PD-L1/PD-1 signalling pathway is a primary mechanism of cancer immune evasion for several reasons. First, and most importantly, this pathway is involved in negative regulation of immune responses of activated T effector cells, found in the periphery. Second, PD-L1 is up-regulated in cancer microenvironments, while PD-1 is also up-regulated on activated tumour infiltrating T cells, thus possibly potentiating a vicious cycle of inhibition. Third, this pathway is intricately involved in both innate and adaptive immune regulation through bi-directional signalling. These factors make the PD-1/PD-L1 complex a central point through which cancer can manipulate immune responses and promote its own progression.

The first immune-checkpoint inhibitor to be tested in a clinical trial was ipilimumab (Yervoy, Bristol-Myers Squibb), a CTLA-4 mAb. CTLA-4 belongs to the immunoglobulin superfamily of receptors, which also includes PD-1, BTLA, TIM-3, and V-domain immunoglobulin suppressor of T cell activation (VISTA). Anti-CTLA-4 mAb is a powerful checkpoint inhibitor which removes "the break" from both naive and antigen-experienced cells. Therapy enhances the antitumor function of CD8+ T cells, increases the ratio of CD8+ T cells to Foxp3+T regulatory cells, and inhibits the suppressive function of T regulatory cells. The major drawback to anti-CTLA-4 mAb therapy is the generation of autoimmune toxicities.

TIM-3 has been identified as another important inhibitory receptor expressed by exhausted CD8+ T cells. In mouse models of cancer, it has been shown that the most dysfunctional tumour-infiltrating CD8+ T cells actually co-express PD-1 and TIM-3.

LAG-3 is another recently identified inhibitory receptor that acts to limit effector T-cell function and augment the suppressive activity of T regulatory cells. It has recently been revealed that PD-1 and LAG-3 are extensively co-expressed by tumour-infiltrating T cells in mice, and that combined blockade of PD-1 and LAG-3 provokes potent synergistic antitumor immune responses in mouse models of cancer.

Cancer patients are often assessed against standard criteria for acknowledging how much a disease impacts a patient's daily living abilities. This assessment is known as the patient's Performance Status (PS). The most popular standardised assessment was developed by the Eastern Cooperative Oncology Group (ECOG) and published in 1982. The ECOG Scale describes a patient's level of functioning, or Performance Status, in terms of their ability to care for themselves, daily activities and physical abilities such as walking or working. It is also a way for medical professionals to track changes in a patient's level of functioning as a result of interventions during cancer treatment. A score of PS 0 indicates the absence of disease, and a score of PS 5 indicates death.

With a median age of 71 years at diagnosis, Pancreatic Ductal Adenocarcinoma (PDAC) is a cancer of the older population. It is projected that by 2030, 70% of PDAC patients in Western countries will be represented by elderly patients (>70 years of age). Despite contributing to the majority of cases of PDAC, elderly patients are consistently under-represented in clinical trials, and treatment of this population of metastatic PDAC is always a challenge.

IMM-101 is an investigational immunomodulator comprising heat killed *Mycobacterium obuense*, typically prepared as a suspension in borate buffered saline which modulates innate and adaptive immune systems, restores Type 1 immune responses and may downregulate Type 2 immune responses. In murine genetically engineered mouse models of pancreatic cancer, IMM-101 prolonged survival. IMM-101 also induced an activation of T cells and cytotoxic CD8+ cells at tumour sites, in the periphery and systemically. It has been demonstrated that the survival benefit was derived from CD8+ T cells from a depletion experiment using a neutralizing antibody. IMM-101 contains microbial-associated molecular patterns (MAMPs) that activate a defined selection of pathogen recognition receptors (PRRs) including toll like receptor (TLR) 1/2 on innate immune cells like dendritic cells (DCs) (Bazzi et al. 2017, Galdon et al. 2019). IMM-101 activation of immature DCs leads to the skewed maturation of activated cDC1, of which activation predominantly induces a type 1 immune response defined by the generation and maturation of IFN-γ, perforin and granzyme producing CTLs (Galdon et al., 2019), required for effective tumour cell killing. IMM-101 induced cDC1 activation also results in the generation of activated IFN-γ producing Th-1 cells NK, NKT and γδ-T cells (Fowler et al., 2014; Galdon et al., 2019), which can kill tumour cells by different mechanisms. Activated γδ-T cells are efficient antigen presenting cells (Moser et al., 2017), which may further boost anti-tumour responses. IMM-101 also activate other innate immune cells, including monocytes, which mature into M1 macrophages (Bazzi et al. 2015) that can enhance anti-tumour responses and prevent the formation of immune-suppressive M2 macrophages.

When using a pancreatic cancer mouse model (mutations in Kras, p53 and Pdx-Cre, known as KPC), the combination of gemcitabine and IMM-101 significantly reduced formation of metastases in the liver and peritoneum. In a phase II trial involving metastatic pancreatic cancer patients, overall survival was significantly improved from 4.4 to 7.0 months with the addition of IMM-101 to gemcitabine therapy and some long-term survivors were seen. In addition, IMM-101 was able to stimulate and mature dendritic cells into activated phenotype through a Type 1 biased stimulation. This Type-1 immune response has also been shown to be a prerequisite for optimal efficacy of immune checkpoint inhibitors (CPI) as the CD103(+) dendritic cells were the only antigen presenting cells transporting intact antigens to the lymph nodes and priming tumour-specific CD8(+) T cells. Using an in vivo bone marrow derived cells (BMDC) transfer model, it has been demonstrated that administration of IMM-101 treated dendritic cells (DCs) induces IFN gamma and IL-17 and enhances DC antigen processing and presentation ability. It was also demonstrated that administration of IMM-101 in combination with PD-1 antibodies reduces tumour burden in syngeneic models of breast and pancreatic cancer, through the significant increase of intratumoral CD8 T cell/Treg ratio in combination with anti PD-1 compared to anti PD-1 alone.

Although these combinations have demonstrated efficacy in the treatment of various cancers, including pancreatic cancer, there are still a lack of defined treatment regimens which are appropriate for those patients who are deemed too vulnerable, too old or unfit to receive efficacious chemotherapy due to their toxicity profiles.

The European Society for Medical Oncology (ESMO) guidelines recommend patients with Metastatic Pancreatic Ductal Adenocarcinoma (mPDAC) and ECOG PS 0 or 1 to receive first line treatment with gemcitabine (Gem) combined with albumin bound paclitaxel (Nab-P), or with infusional 5-fluorouracil (5-FU), leucovorin/folinic acid (LV), irinotecan and oxaliplatin (FOLFIRINOX). Less fit patients (PS 2) or those over 70 years old generally receive gemcitabine monotherapy, optionally in combination with nab-paclitaxel for a short period (due to side effects), or are offered other less toxic regimens, including best supportive care in those with worse PS or comorbidities.

Patients that are PS 2 or older than 70 years of age have been the focus of several studies. Recently, Macarulla et al (Pancreas. 2020; 49(3):393-407), evaluated different regimens of Gemcitabine in combination with nab-Paclitaxel (Gem/Nab-P) in patients with metastatic PDAC or locally advanced PDAC that were PS 2. Over 100 patients were evaluated, and the study determined that Gem/Nab-P was well tolerated in these patients at a dose of either 100 or 125 mg/square metre nab-paclitaxel and Gemcitabine 1000 mg/square metre, administered at Day 1, 8 and 15 every 28 days. Additionally, this regimen showed efficacy although the findings remain to be validated in larger patient groups.

As such, FOLFIRINOX (a combination of folinic acid, fluorouracil, irinotecan hydrochloride and oxaliplatin), nab-paclitaxel (Abraxane®) plus gemcitabine are the preferred first line treatments for metastatic pancreatic ductal adenocarcinoma (mPDAC) patients with an ECOG Performance Status of 0 and 1 only. These treatments are often contraindicated for patients in many countries with a score of PS2 or above, due to their toxicity profile. However, almost 50% of patients presenting with de novo metastatic disease are of a lower performance score and have very limited options in terms of active intervention. Single agent chemotherapeutics such as gemcitabine confer a modest benefit, at best, in the trade-off between an already limited quality of life and coping with a toxic regimen that may worsen the patient's health. This subgroup of patients are traditionally poorly served in the clinical trial setting due to these inclusion and exclusion criteria.

Therefore, a novel tolerable combination therapy is urgently needed for such PS 1-, 2, 3 and 4 patients.

SUMMARY OF THE INVENTION

The present invention provides an effective method of treating, reducing, inhibiting or controlling cancer in a subject, by administering a *Mycobacterium* preparation to a specific class of patients as clinically classified according to the ECOG Scale, or classified as not being fit enough to tolerate a number of chemotherapy regimens.

In a first aspect of the invention, there is provided a non-pathogenic non-viable whole cell *Mycobacterium* for use in the treatment, reduction, inhibition or control of cancer in a subject, wherein the subject is clinically classified as having a performance status of 1-, 2, 3 or 4 according to the ECOG Scale.

In a second aspect of the invention, there is provided a non-pathogenic non-viable whole cell *Mycobacterium* for use in the treatment, reduction, inhibition or control of cancer in a subject, wherein the subject is a human patient classified as not being of an age and/or sufficiently fit to tolerate two or more chemotherapy regimens and, optionally, are considered eligible to receive gemcitabine and nab-paclitaxel.

In a third aspect of the invention, there is provided a non-pathogenic non-viable *Mycobacterium* for use in the treatment, reduction, inhibition or control of cancer in a subject wherein said subject is a human patient and wherein the non-pathogenic non-viable *Mycobacterium* is *M. obuense* NCTC 13365, the human subject is simultaneously, separately or sequentially administered a nucleoside metabolic inhibitor, preferably gemcitabine, and further administered one or more checkpoint inhibitors, preferably pembrolizumab, and wherein the subject is clinically classified as having a performance status of 1-, 2, 3 or 4 according to the Eastern Cooperative Oncology Group (ECOG) Scale.

In a fourth aspect of the invention, there is provided a method of treating, reducing, inhibiting or controlling cancer in a subject, wherein said subject is a human patient and wherein said method comprises simultaneously, separately or sequentially administering to the subject (i) one or more therapeutic agents and/or cancer treatments and (ii) a non-pathogenic non-viable *Mycobacterium*, wherein said method results in enhanced therapeutic efficacy relative to administration of one or more therapeutic agents and/or cancer treatments alone, and wherein the human patient is clinically classified as having a performance status of 1-, 2, 3 or 4 according to the Eastern Cooperative Oncology Group (ECOG) Scale.

In a fifth aspect of the invention, there is provided a method of treating, reducing, inhibiting or controlling cancer in a subject, wherein said subject is a human patient and wherein said method comprises simultaneously, separately or sequentially administering to the subject (i) one or more therapeutic agents and/or cancer treatments and (ii) a non-pathogenic non-viable *Mycobacterium*, wherein said method results in enhanced therapeutic efficacy relative to administration of one or more therapeutic agents and/or cancer treatments alone, and wherein the human patient is clinically classified as having a performance status of 1-, 2, 3 or 4 according to the Eastern Cooperative Oncology Group (ECOG) Scale, wherein the human patient is classified as not being of an age and/or sufficiently fit to tolerate two or more chemotherapy regimens and, optionally, are considered eligible to receive gemcitabine and nab-paclitaxel.

In a sixth aspect of the invention, there is provided a non-pathogenic non-viable *Mycobacterium* for use in the treatment, reduction, inhibition or control of cancer in a subject, wherein the subject is clinically classified as having a performance status of 0, 1, 1-, 2, 2+, 3, 4, according to the ECOG Scale, wherein the subject is a human patient is 70 or more years old.

The present invention therefore provides a pathogenic non-viable whole cell *Mycobacterium* for use in the treatment, reduction, inhibition or control of cancer in a subject, together with a method of treating said cancer by administration of said *Mycobacterium*. The inventors have unexpectedly found that the administration of *Mycobacterium* to a specific category of patients who have been previously contraindicated according to their ECOG Score and/or age, is particularly effective in the course of chemotherapeutic treatment. This is contrary to historical findings which suggest that this group of patients is not capable or tolerant enough to withstand chemotherapeutic treatment.

DESCRIPTION OF THE DRAWINGS

The invention is described with reference to the following drawings, in which.

DETAILED DESCRIPTION OF THE INVENTION

Figure 1:
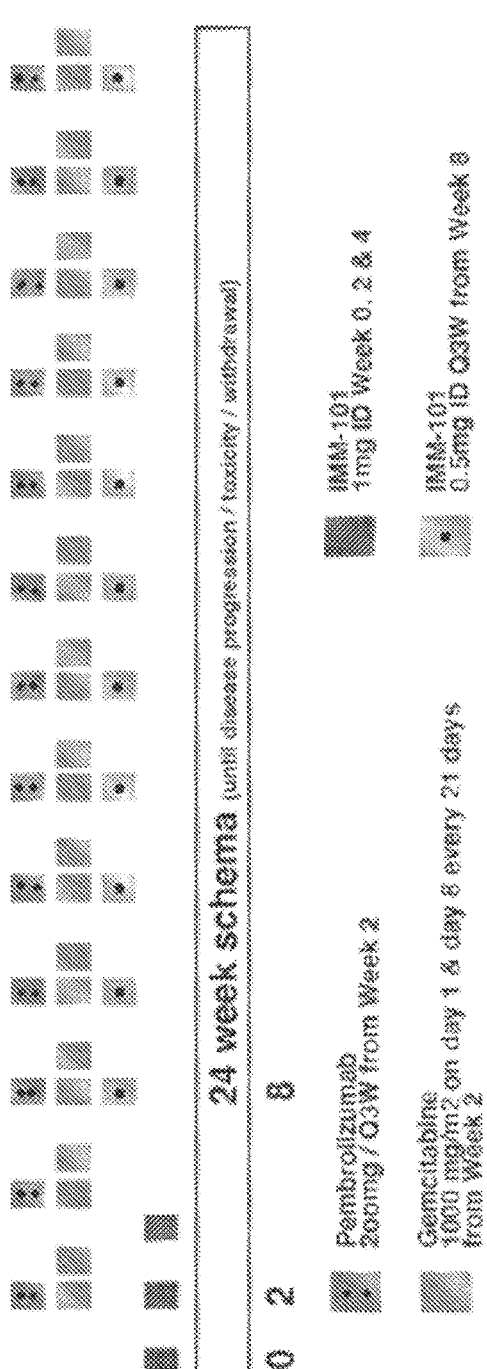
FIG. 1 shows the treatment schedule for IMM-101; 1 mg intra-dermal on Weeks 2 and 4, then 0.5 mg intradermal Q3W from Week 8. Pembrolizumab; 200 mg IV Q3W from Week 2. Gemcitabine; 1000 mg/m$^2$ intravenously on day 1 and day 8 every 21 days from Week 2 under Example 1.

The invention provides a non-pathogenic non-viable whole cell *Mycobacterium* for use in the treatment, reduction, inhibition or control of cancer in a subject, wherein the subject is clinically classified as having a performance status of 1-, 2, 3 or 4 according to the ECOG Scale. Optionally, said human patient is classified as not being of an age and/or sufficiently fit to tolerate two or more chemotherapy regimens. They may also be considered eligible to receive gemcitabine and nab-paclitaxel. It is based upon the discovery that the administration of a *Mycobacterium* to a patient who is clinically classified as unfit to tolerate a standardised chemotherapeutic regime is unexpectedly responsive and/or is able to tolerate chemotherapeutic treatment.

In order that the present invention may be more readily understood, certain terms are first defined. Additional definitions are set forth throughout the detailed description.

The terms "tumour," "cancer" and "neoplasia" may be used interchangeably and refer to a cell or population of cells whose growth, proliferation or survival is greater than growth, proliferation or survival of a normal counterpart cell, e.g. a cell proliferative or differentiative disorder. Typically, the growth is uncontrolled. The term "malignancy" refers to invasion of nearby tissue. The term "metastasis" refers to spread or dissemination of a tumour, cancer or neoplasia to other sites, locations or regions within the subject, in which the sites, locations or regions are distinct and/or distant from the primary tumour or cancer.

The term "non-metastatic" refers to where, relative to a primary tumour, node or cancer in a patient, there are no distant metastases or residual disease, as determined by CT, MRI or Positron emission tomography (PET) with 2-deoxy-2-[fluorine-18] fluoro-D-glucose (18F-FDG) scanning.

The terms "Programmed Death 1," "Programmed Cell Death 1," "Protein PD-1," "PD-1," and "PD1," are used interchangeably, and include variants, isoforms, species homologs of human PD-1, and analogs having at least one common epitope with PD-1. A "checkpoint inhibitor" is an agent which acts on surface proteins which are members of either the TNF receptor or B7 superfamilies, including agents which bind to negative co-stimulatory molecules, selected from a cell, protein, peptide, antibody, bispecific antibody, ADC (antibody-drug conjugate), Fab fragment (Fab), F(ab')2 fragment, diabody, triabody, tetrabody, pro-body, single-chain variable region fragment (scFv), disulfide-stabilized variable region fragment (dsFv), or other antigen binding fragment thereof, directed against CTLA-4, PD-1, PD-L1, PD-L2, B7-H3, B7-H4, B7-H6, A2AR, IDO, TIM-3, BTLA, VISTA, TIGIT, LAG-3, CD40, KIR, CEACAM 1, GARP, PS, CSF1 R, CD94/NKG2A, TDO, TNFR, DcR3, CD27, CD28, CD40, CD122, CD137, 0X40, GITR, ICOS and combinations thereof. A "blocking agent" is an agent which either binds to the above costimulatory molecules and/or their respective ligands. "Checkpoint inhibitor" and "blocking agent" can be used interchangeably throughout. The inhibitor is preferably an antibody or antigenic-binding molecule that targets an antigenic site on the surface proteins. For example, the inhibitor is an antibody that targets an antigenic site on PD-L1, or PD-1 or CTLA-4.

As used herein, "sub-therapeutic dose" means a dose of a therapeutic compound (e.g., an antibody) or modality or duration of therapy which is lower than the usual or typical dose of the therapeutic compound or therapy or modality of shorter duration, when administered alone for the treatment of cancer.

The term "therapeutically effective amount" is defined as an amount of one or more therapeutic agents or modalities, including checkpoint inhibitors, in combination with an immunomodulator, that preferably results in a decrease in severity of disease symptoms, an increase in frequency and duration of disease symptom-free periods, or a prevention of impairment or disability due to the disease affliction. The terms "effective amount" or "pharmaceutically effective amount" refer to a sufficient amount of an agent to provide the desired biological or therapeutic result. That result can be reduction, amelioration, palliation, lessening, delaying, and/or alleviation of one or more of the signs, symptoms, or causes of a disease, or any other desired alteration of a biological system. In reference to cancer, an effective amount may comprise an amount sufficient to cause a tumour to shrink and/or to decrease and/or stabilise the growth rate of the tumour (such as to suppress tumour growth) or to prevent or delay other unwanted cell proliferation. In some embodiments, an effective amount is an amount sufficient to delay development, or prolong survival or induce stabilisation of the cancer or tumour.

In some embodiments, a therapeutically-effective amount is an amount sufficient to prevent or delay recurrence. A therapeutically-effective amount can be administered in one or more administrations. The therapeutically-effective amount of one or more therapeutic agents or modalities or combinations thereof, may result in one or more of the following: (i) reduce the number of cancer cells; (ii) reduce tumour size; (iii) inhibit, retard, slow to some extent and preferably stop cancer cell infiltration into peripheral organs;

(iv) inhibit (i.e., slow to some extent and preferably stop) tumour metastasis; (v) inhibit tumour growth; (vi) prevent or delay occurrence and/or recurrence of tumour; and/or (vii) relieve to some extent one or more of the symptoms associated with the cancer. For example, for the treatment of tumours, a "therapeutically effective dosage" may induce tumour shrinkage by at least about 5% relative to baseline measurement, such as at least about 10%, or about 20%, or about 60% or more. The baseline measurement may be derived from untreated subjects. A therapeutically-effective amount of a therapeutic compound can decrease tumour size, or otherwise ameliorate symptoms in a subject. One of ordinary skill in the art would be able to determine such amounts based on such factors as the subject's size, the severity of the subject's symptoms, and the particular composition or route of administration selected.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells.

The terms "effective amount" or "pharmaceutically effective amount" refer to a sufficient amount of an agent to provide the desired biological or therapeutic result. That result can be reduction, amelioration, palliation, lessening, delaying, and/or alleviation of one or more of the signs, symptoms, or causes of a cancer or any other desired alteration of a biological system. In reference to cancer, an effective amount may comprise an amount sufficient to cause a tumour to shrink and/or to decrease the growth rate of the tumour (such as to suppress tumour growth) or to prevent or delay other unwanted cell proliferation. In some embodiments, an effective amount is an amount sufficient to delay development, or prolong survival or induce stabilisation of the cancer or tumour. Preferably, therapeutic efficacy is measured by a decrease or stabilisation of tumour size of one or more said tumours, as defined by RECIST 1.1, including stable diseases (SD), a complete response (CR) or partial response (PR) of the target tumour; and/or stable disease (SD), partial response (PR) or complete response (CR) of one or more non-target tumours. Alternatively, therapeutic efficacy is assessed by Immune Related Response Criteria (irRC), iRECIST or irRECIST, and other metrics known or developed for determining the response to therapies, as would be known to the skilled person.

The term "checkpoint inhibitor" or "immunomodulator" or "immunotherapy" may further include use of a cell, virus, lysate, vector, gene, mRNA, DNA, nucleic acid, protein, polypeptide, peptide, antibody, bispecific antibody, multi-specific antibody, ADC (antibody-drug conjugate), Fab fragment (Fab), F(ab')2 fragment, diabody, triabody, tetrabody, probody, single-chain variable region fragment (scFv), disulfide-stabilized variable region fragment (dsFv), or other antigen binding fragment thereof, in practising the invention. The inhibitor is preferably an antibody.

The term "antibody" as referred to herein includes whole antibodies and any antigen-binding fragment (i.e., "antigen-binding portion") or single chains thereof.

By "non-viable", it is meant that the *Mycobacterium* have been microbiologically inactivated through certain means of cell-killing. Methods to enable or enforce such non-viability may include heat-killing, extended freeze-drying (Tolerys SA), irradiation by gamma waves or electron beam, or subjecting the mycobacteria to chemicals such as formaldehyde. Such preparation during manufacture would mean the organism is not associated with side-effects known from delivering live or attenuated organisms.

The term "treatment" or "therapy" refers to administering an active agent with the purpose to cure, heal, alleviate, relieve, alter, remedy, ameliorate, improve, or affect a condition (e.g., a disease), the symptoms of the condition, or to prevent or delay the onset of the symptoms, complications, biochemical indicia of a disease, or otherwise arrest or inhibit further development of the disease, condition, or disorder in a statistically significant manner.

As used herein, the term "subject" or "patient" is intended to include human and non-human animals. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo.

As used herein, the terms "concurrent administration" or "concurrently" or "simultaneous" mean that administration occurs on the same day. The terms "sequential administration" or "sequentially" or "separate" mean that administration occurs on different days.

"Simultaneous" administration, as defined herein, includes the administration of the non-pathogenic non-viable *Mycobacterium* and one or more therapeutic agents or modalities, including checkpoint inhibitor therapy, within about 2 hours or about 1 hour or less of each other, even more preferably at the same time.

"Separate" administration, as defined herein, includes the administration of the non-pathogenic non-viable *Mycobacterium* and one or more therapeutic agents or modalities, including checkpoint inhibitor therapy, more than about 12 hours, or about 8 hours, or about 6 hours or about 4 hours or about 2 hours apart.

"Sequential" administration, as defined herein, includes the administration of the non-pathogenic non-viable *Mycobacterium* and one or more therapeutic agents or modalities, including checkpoint inhibitor therapy or chemotherapeutic agents, each in multiple aliquots and/or doses and/or on separate occasions. The non-pathogenic non-viable *Mycobacterium* may be administered to the patient after before and/or after administration of the one or more therapeutic agents or modalities, including checkpoint inhibitor therapy. Alternatively, the non-pathogenic non-viable *Mycobacterium* is continued to be applied to the patient after treatment with one or more therapeutic agents or modalities, including checkpoint inhibitor therapy.

As used herein, "treatment" encompasses the prevention, reduction, control and/or inhibition of a neoplastic disease, including the regression or stabilization of a primary tumour and/or the regression or stabilization of one or metastases, or the prevention or inhibition of one or more metastases or micrometastases.

The use of the alternative (e.g., "or") should be understood to mean either one, both, or any combination thereof of the alternatives. As used herein, the indefinite articles "a" or "an" should be understood to refer to "one or more" of any recited or enumerated component.

As used herein, "about" means within an acceptable error range for the particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" can mean a range of up to 20%. When particular values are provided in the application and claims, unless otherwise stated, the meaning of "about" should be assumed to be within an acceptable error range for that particular value.

As part of the invention, the subject is classed as having a performance status of 1-, 2, 3 or 4 according to the ECOG scale. The ECOG scale may also be known as the Zubrod Scale or the WHO Scale, and is therefore interchangeable with such terms. "Performance Status" and "PS" are also used interchangeably throughout. The ECOG scale is from PS 0 to PS 5, as detailed in the table below. In some embodiments, a value of PS1—represents an integer and status between PS1 and PS2, whereby the patient is not exhibiting all aspects of behaviour as severe as PS2, and is not exhibiting all aspects of behaviour categorised as PS1. Similarly, a designation of PS 2+ represents an integer and status between PS 2 and PS 3. A further clinical classification method of performance status is also known as the Karnofsky Scale, which is from 0 to 100, whereby 100 is the absence of disease and 0 is death.

Two clinical observers are usually required to assess performance status. If there is any discrepancy between the two scores, the highest (worst) assessment will be used. Performance status may also be assigned in clinical practice, according to the patients' tumour burden, pain levels and other parameters, as known to those skilled in the art.

| Karnofsky Status | Karnofsky Grade | ECOG Grade | ECOG Status |
|---|---|---|---|
| Normal, no complaints | 100 | 0 | Fully active, able to carry on all pre-disease performance without restriction |
| Able to carry on normal activities. Minor signs or symptoms of disease | 90 | 0 | Restricted in physically strenuous activity but ambulatory and able to carry out work of a light or sedentary nature, e.g., light housework, office work |
| Normal activity with effort | 80 | 1 | Restricted in physically strenuous activity but ambulatory and able to carry out work of a light or sedentary nature, e.g., light housework, office work |
| Care for self. Unable to carry on normal activity or to do active work | 70 | 1 | Ambulatory and capable of all selfcare but unable to carry out any work activities. Up and about more than 50% of waking hours |

-continued

| Karnofsky Status | Karnofsky Grade | ECOG Grade | ECOG Status |
|---|---|---|---|
| Requires occasional assistance, but able to care for most of his needs | 60 | 2 | Ambulatory and capable of all selfcare but unable to carry out any work activities. Up and about more than 50% of waking hours |
| Requires considerable assistance and frequent medical care | 50 | 2 | Capable of only limited selfcare, confined to bed or chair more than 50% of waking hours |
| Disabled. Requires special care and assistance | 40 | 3 | Capable of only limited selfcare, confined to bed or chair more than 50% of waking hours |
| Severely disabled. Hospitalisation indicated though death non-imminent | 30 | 3 | Completely disabled. Cannot carry on any selfcare. Totally confined to bed or chair |
| Very sick. Hospitalisation necessary. Active supportive treatment necessary | 20 | 4 | Completely disabled. Cannot carry on any selfcare. Totally confined to bed or chair |
| Moribund | 10 | 4 | Completely disabled. Cannot carry on any selfcare. Totally confined to bed or chair |
| Dead | 0 | 5 | Dead |

A Karnofsky Scale value of 60 or above may be equivalent to an ECOG Scale reading of PS 2, 3, 4 or 5. Alternatively, the subject or human patient targeted for administration with the *Mycobacterium* can be alternatively classified as not being sufficiently fit to tolerate two or more chemotherapy regimens. A subject classified as not being of an age and/or sufficiently fit to tolerate two or more chemotherapy regimens and, optionally, are considered eligible to receive gemcitabine and nab-paclitaxel, may be considered to be equivalent to a subject or patient with a score of PS 2, 3 or 4 according to the ECOG scale, suitably a score of PS 2, or equivalent to a subject or human patient with a score of 60 or above according to the Karnofsky Scale, e.g. 70.

A chemotherapy regimen according to the present invention is an administration of a chemotherapeutic agent or multiple chemotherapeutic agents, optionally simultaneously, separately or sequentially with any other therapeutic agent. The regimen may be repeated more than once a day, more than once a week, more than once a month, or more than once a year. The chemotherapeutic agent may be cytotoxic, which is defined as likely to cause cellular death by interfering in one or more cellular mechanisms.

*M. vaccae* and *M. obuense* have been shown to induce a complex immune response in the host. Treatment with these preparations will stimulate innate and type-1 immunity, including Th1 and macrophage activation and cytotoxic cell activity. They also independently down-regulate inappropriate Th2 responses via immunoregulatory mechanisms. In relation to cancer, it is likely that the formation of IFN-γ producing CTLs is the most important result from IMM-101 treatment, since the observed anti-tumour effect of IMM-101 could be completely abrogated by the depletion of CD8+ T cells in a pancreas cancer model.

IMM-101's ability to activate macrophages may not only assist in the activation of DCs through the release of pro-inflammatory macrophage-derived cytokines (such as IL-12 required for skewing DCs into Type 1 immune responses), but may also be of importance for changing tumour associated immunosuppressive type 2 macrophages into tumour aggressive type 1 macrophages. This latter feature was shown for a similar heat-killed *mycobacterium*, *M. indicus pranii*.

An important feature of IMM-101 is its ability to activate and mature DCs into a sub-class of dendritic cells known as cDC1s (i.e. DCs that are required for Type 1 immune responses). It has been shown that activation of sufficient numbers of cDC1s is a prerequisite for CPIs to be effective.

Preoperative short time administration of checkpoint inhibitors in microsatellite instability (MSI) high colorectal cancers has been shown to induce high rates of pathological regression. In a recently presented small explorative phase II study (Chalabi et al. 2018, *immunotherapy of cancer* 29:8), six weeks of preoperative administration of the CTLA-4 antibody ipilimumab and the PD-1 antibody nivolumab was shown to result in a complete or subtotal pathological remission, suggesting that neoadjuvant therapies could be particularly efficacious for some cancer presentations.

The present invention also provides a protocol to use IMM-101 as a surprisingly favourable neoadjuvant treatment, or adjuvant treatment, or peri-adjuvant treatment, with or without the use of other chemotherapy agents, to improve the unfavourable prognosis of patients intended to undergo tumour resection surgery or checkpoint inhibitor therapy for cancer. Such patients may include those with colorectal cancer, or patients with mismatch repair-deficient (dMMR) cancers with or without microsatellite instability (MSI).

In a further aspect of the invention, the cancer is determined as being microsatellite instability (MSI) high, as measured by a PCR-based assay and/or where the cancer is subject to IHC staining for analysis of DNA mismatch repair (MMR) protein expression. In one aspect of the present invention the non-pathogenic, non-viable *Mycobacterium* comprises a whole cell, non-pathogenic heat-killed *Mycobacterium*. Examples of mycobacterial species for use in the present invention include *M. vaccae, M. thermoresistibile, M. flavescens, M. duvalii, M. phlei, M. obuense, M. parafortuitum, M. sphagni, M. aichiense, M. rhodesiae, M. neoaurum, M. chubuense, M. tokaiense, M. komossense, M. aurum, M. w, M. tuberculosis, M. microti; M. africanum; M. kansasii, M. marinum; M. simiae; M. gastri; M. nonchromogenicum; M. terrae; M. triviale; M. gordonae; M. scrofulaceum; M. paraffinicum; M. intracellulare; M. avium; M. xenopi; M. ulcerans; M. diernhoferi, M. smegmatis; M. thamnopheos; M. flavescens; M. fortuitum; M. peregrinum;*

*M. chelonei; M. paratuberculosis; M. leprae; M. lepraemurium* and combinations thereof.

The non-viable, non-pathogenic *Mycobacterium* is preferably selected from *M. vaccae*, including the strain deposited under accession numbers NCTC 11659 and associated designations such as SRL172, SRP299, IMM-201, DAR-901, and the strain as deposited under ATCC 95051 (Vaccae™), *M. obuense, M. paragordonae* (strain 49061), *M. parafortuitum, M. paratuberculosis, M. brumae, M. aurum, M. indicus pranii, M. w, M. manresensis, M. kyogaense* (as deposited under DSM 107316/CECT 9546), *M. phlei, M. smegmatis, M. tuberculosis* Aoyama B or H37Rv, RUTI, MTBVAC, BCG, VPM1002BC, SMP-105, mifamurtide or Z-100 and combinations thereof, preferably the strain of *Mycobacterium obuense* deposited under the Budapest Treaty under accession number NCTC 13365.

In another most preferred embodiment, the non-viable *Mycobacterium* is *M. vaccae*, including that deposited under NCTC 11569, or *M. obuense*, such as that deposited under NCTC 13365. More preferably the non-pathogenic non-viable *Mycobacterium* is a rough variant. Preferably, the non-pathogenic non-viable *Mycobacterium* is heat-killed.

In preferred embodiments of the invention, the non-pathogenic, non-viable *Mycobacterium* is the rough variant, preferably the rough variant of *M. obuense*.

In other embodiments of the invention, the non-pathogenic non-viable *Mycobacterium* is the rough variant and/or whole cell, preferably the rough strain of *Mycobacterium obuense* deposited under the Budapest Treaty under accession number NCTC 13365.

In another embodiment of the invention, the non-pathogenic non-viable *Mycobacterium* has been inactivated by heat such as autoclaving, extended freeze drying, chemical exposure such as formaldehyde, or irradiation such as gamma irradiation or e-beam.

In another embodiment of the invention, the non-pathogenic non-viable *Mycobacterium* does not include BCG in live, attenuated form.

In a further embodiment, the non-pathogenic non-viable *Mycobacterium* is the rough variant and/or a presented as a fraction, fragment, sub-cellular component, lysate, homogenate, sonicate, or substantially in whole cell form.

In preferred embodiments of the invention, the non-pathogenic, non-viable *Mycobacterium*, suitably *Mycobacterium obuense*, is in a substantially whole cell form, such as where more than 50% or more of the mycobacteria in suspension are greater than 1 to 10 microns in diameter, as measured by laser diffraction (e.g. D50 value or mean particle size), or is in a form which has not been exposed to high pressure processing or other conditions to induce substantial cell lysis.

As would be understood by the skilled person, rough variants of *M. obuense*, for example, would lack cell surface-associated glycopeptidolipids (GPL) resulting in a characterised rough morphology with non-motile and non-biofilm-forming properties, as described in Roux et al. 2016, Open Biol 6: 160185. The amount of *Mycobacterium* administered to the patient in the present invention would be sufficient to elicit a protective immune response in the patient such that the patient's immune system would be able to mount an effective immune response.

The amount of *Mycobacterium* administered to the patient is sufficient to elicit a protective immune response in the patient such that the patient's immune system is able to mount an effective immune response to the cancer or tumour. In certain embodiments of the invention, there is provided a containment means comprising the effective amount of non-viable *Mycobacterium* for use in the present invention, which typically may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms. The effective amount of non-viable *Mycobacterium* for use in the present invention may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms. Most preferably the amount of non-viable whole cell *Mycobacterium* for use in the present invention is from $10^7$ to $10^9$ cells or organisms.

Typically, the composition according to the present invention may be administered at a dose of from $10^8$ to $10^9$ cells for human and animal use. Alternatively, the dose is from 0.0001 mg to 5 mg or 0.001 mg to 5 mg organisms, preferably 0.01 mg to 2 mg or 0.1 mg to 2 mg organisms, such as where the dose is approximately 0.5 mg or 1 mg or 0.5 mg or 1 mg organisms. The dose may be prepared as either a suspension or dry preparation.

In another embodiment, the non-pathogenic non-viable *Mycobacterium* is to be administered into the skin of the human patient via a microneedle device comprising a plurality of microneedles, as disclosed in WO2021/136933, incorporated herein by reference. Other preferred microneedle devices for use according to the invention include: North Carolina State University (as described in WO2017/151727), Debioject microneedle (Debiotech, Switzerland), Micronject600 (NaoPass, Israel, as described in WO2008/047359), Nanopatch (Vaxxas, USA), SOFUSA (Kimberly-Clark, USA, as described in WO2017/189259 and WO2017/189258), Micron Biomedical's dissolving microarray, and the MIMIX dissolving, controlled release microarray (Vaxess, USA).

*M. vaccae* and *M. obuense* induce a complex immune response in the host. Treatment with these preparations will stimulate innate and type-1 immunity, including Th1 and macrophage activation and cytotoxic cell activity. They also independently down-regulate inappropriate Th2 responses via immunoregulatory mechanisms. This restores the healthy balance of the immune system.

In certain embodiments of the invention, the amount of non-pathogenic non-viable *Mycobacterium* administered is between 0.0001 mg and 1 mg per unit dose, optionally wherein the unit dose is administered on two or more separate occasions separated by at least 7 days or more, such as administration on each of day 0, day 14 (+/−1, 3 or 5 days or more), and optionally day 30 (+/−5, 7 or 10 days or more) or day 45 (+/−7, 10 or 14 days or more).

In some embodiments, the amount of non-pathogenic non-viable *Mycobacterium* administered may be from 0.0001 mg to 1 mg per dose wherein the dose is administered at the same or different dose 1, 2, 3, 4, 5, 6, 10 or 20 or more times over a number of days, weeks, or months, suitably wherein the *Mycobacterium* is *M. obuense*.

In other embodiments of the invention, the amount of non-pathogenic non-viable *Mycobacterium* administered may be from 0.0001 mg to 1 mg per dose, wherein the dose initially comprises one injection of 1 mg into one deltoid, or two injections of 0.5 mg in each deltoid, or two injections of 1.0 mg in each deltoid, followed by a second dose of either 0.5 or 1.0 mg 7 or 14 days or more later.

In other embodiments of the invention, the amount of non-pathogenic non-viable *Mycobacterium* administered may be from 0.0001 mg to 1 mg per dose, wherein the dose initially comprises one injection of 1 mg into one deltoid, or two injections of 0.5 mg in each deltoid, or two injections of 1.0 mg in each deltoid, followed by a second dose of either 0.5 or 1.0 mg 7 or 14 days or more later.

In certain embodiments of the invention, the amount of non-pathogenic non-viable *Mycobacterium* administered is between 0.0001 mg and 1 mg per unit dose, such as between about 0.5 and 1 mg, wherein the unit dose is administered on two or more separate occasions separated by at least 7 days or more, prior to surgery, such as administration on each of day −35, day −21 and day −5 relative to (i.e. prior to) surgery, optionally where the −35 day dose is 1 mg, the −21 day dose is 0.5 mg and the −5 day dose is 0.5 mg. The checkpoint therapy, such as an anti-PD-L1 mab, suitably atezolizumab, pembrolizumab or cemiplimab, may be administered on the same day or in between the unit dose of said *Mycobacterium*, such as day −28 and day −7, relative to (i.e. prior to) said surgery.

In further embodiments, the non-pathogenic non-viable *Mycobacterium* is administered to the subject as a first line treatment, optionally simultaneously, separately or sequentially with administration of one or more therapeutic agents or cancer treatments. A first line treatment may also be known as a primary treatment, and is typically administered to the subject or patient as a first treatment or therapy after initial diagnosis. Other therapeutic agents may include any pharmaceutical agents typically used to treat cancer, control cancer, provide pain relief or act prophylactically against any cancer-related pathologies, such as steroids, bisphosphonates and NSAIDs. Preferably, cancer treatments may include, but are not limited to, surgery, radiotherapy, preferably targeted radiotherapy such as stereotactic body radiation therapy (e.g. Cyberknife®), and chemotherapy. Chemotherapy may include administration of, but is not limited to, anti-neoplastics, anti-metabolites, microtubule inhibitors, nucleoside metabolic inhibitors and immunogenic agents. Preferred chemotherapeutic agents include FOLFIRINOX, Abraxane® (nab-paclitaxel), gemcitabine and pembrolizumab, preferably in multiple combinations. Preferably, a nucleoside metabolic inhibitor is administered, most preferably gemcitabine. Preferably, a microtubule inhibitor is administered, most preferably Abraxane (nab-paclitaxel).

Preferred chemotherapeutic agents include, but are not limited to, one or more cytotoxic chemotherapeutic agents selected from: bevacizumab, cyclophosphamide, methotrexate, 5-fluorouracil, doxorubicin, mustine, vincristine, procarbazine, prednisolone, bleomycin, vinblastine, dacarbazine, etoposide, cisplatin, epirubicin, capecitabine, leucovorin, folinic acid, carboplatin, oxaliplatin, gemcitabine, FOLFIRINOX, FOLFOX, FOLFIRI, mFOLFIRINOX, NALIRIFOX, paclitaxel, nab-paclitaxel, pemetrexed, irinotecan, temozolomide and combinations thereof, wherein said one or more agents is administered intratumorally, intraarterially, intravenously, intravascularly, intrapleuraly, intraperitoneally, intratracheally, intranasally, pulmonarily, intrathecally, intramuscularly, endoscopically, intralesionally, percutaneously, subcutaneously, regionally, stereotactically, orally or by direct injection or perfusion, optionally wherein the human patient demonstrated a partial response or stable disease.

In further embodiments, the non-pathogenic non-viable whole cell *Mycobacterium* is administered to the subject as a first or second line or maintenance treatment, simultaneously, separately or sequentially with administration of both gemcitabine and nab-paclitaxel, optionally subsequent to previous FOLFIRINOX, FOLFOX, FOLFIRI, mFOLFIRINOX, NALIRIFOX or similar therapy. This maintenance treatment is particularly applicable to patients with metastatic pancreatic ductal adenocarcinoma.

In a further embodiment, the non-pathogenic non-viable *Mycobacterium* is administered to the subject as a first or second line or maintenance treatment, simultaneously, separately or sequentially with administration of gemcitabine and optionally one or more checkpoint inhibitors, suitably pembrolizumab, optionally subsequent to FOLFIRINOX, FOLFOX, FOLFIRI, mFOLFIRINOX, NALIRIFOX or similar therapy. This maintenance treatment is particularly applicable to patients with metastatic pancreatic ductal adenocarcinoma.

In further embodiments, the non-pathogenic non-viable *Mycobacterium* is administered to the subject as a first or second line or maintenance treatment, simultaneously, separately or sequentially with administration of both gemcitabine and nab-paclitaxel, optionally subsequent to a partial response or stabilisation under FOLFIRINOX, FOLFOX, FOLFIRI, mFOLFIRINOX, NALIRIFOX or similar therapy. This maintenance treatment is particularly applicable to patients with metastatic pancreatic ductal adenocarcinoma.

In a further embodiment, the non-pathogenic non-viable *Mycobacterium* is administered to the subject as a first or second line or maintenance treatment, simultaneously, separately or sequentially with administration of both gemcitabine and one or more checkpoint inhibitors, suitably pembrolizumab, optionally subsequent to an adequate response under FOLFIRINOX, FOLFOX, FOLFIRI, mFOLFIRINOX, NALIRIFOX or similar therapy. This maintenance treatment is particularly applicable to patients with metastatic pancreatic ductal adenocarcinoma.

In a further embodiment, the non-pathogenic non-viable *Mycobacterium* is administered to the subject as a first or second line or maintenance treatment, simultaneously, separately or sequentially with administration of both gemcitabine and one or more checkpoint inhibitors, suitably pembrolizumab, optionally subsequent to FOLFIRINOX, FOLFOX, FOLFIRI, mFOLFIRINOX, NALIRIFOX or similar therapy. This maintenance treatment is particularly applicable to patients with metastatic pancreatic ductal adenocarcinoma.

In further embodiments, the non-pathogenic non-viable *Mycobacterium* is administered to the subject as a first or second line or maintenance treatment, simultaneously, separately or sequentially with administration of both gemcitabine and nab-paclitaxel, optionally subsequent to an adequate response under FOLFIRINOX, FOLFOX, FOLFIRI, mFOLFIRINOX, NALIRIFOX or similar therapy. This maintenance treatment is particularly applicable to patients with metastatic pancreatic ductal adenocarcinoma.

In a further embodiment, the non-pathogenic non-viable *Mycobacterium* is administered to the subject as a first or second line or maintenance treatment, simultaneously, separately or sequentially with administration of both gemcitabine and one or more checkpoint inhibitors, suitably pembrolizumab, optionally subsequent to a partial response or stabilisation under FOLFIRINOX, FOLFOX, FOLFIRI, mFOLFIRINOX, NALIRIFOX or similar therapy. This maintenance treatment is particularly applicable to patients with metastatic pancreatic ductal adenocarcinoma.

In a preferred embodiment, the non-pathogenic non-viable *Mycobacterium* is administered to the subject as first line treatment for patients that have been recently diagnosed with metastatic ductal adenocarcinoma of the pancreas, who have not yet been treated with any agent, except for surgery and/or radiotherapy as an adjuvant therapy, and have an ECOG performance status of 2 or are over 70 years of age and are, in the opinion of the clinician, considered eligible to receive gemcitabine and nab-paclitaxel.

In a preferred embodiment, is provided a regimen for patients who are currently effectively excluded from a first line therapy such as FOLFIRINOX (or FOLFOX, FOLFIRI, mFOLFIRINOX, NALIRIFOX or similar), if they are PS 2 or over 70 years old and deemed by their doctor as not suitable for FOLFIRINOX.

In further embodiments, the non-pathogenic non-viable *Mycobacterium* is administered to the subject as a first or second line or maintenance treatment, simultaneously, separately or sequentially with administration of both gemcitabine and nab-paclitaxel, where said nab-paclitaxel is provided at a dose of between 100 and 125 mg/m² and administered as an i.v. infusion over about 30 minutes followed by Gemcitabine 1000 mg/m² as a 30-minute i.v. infusion on Day 1, Day 8 and Day 15 of a 28-day cycle. This maintenance treatment is particularly applicable to patients with metastatic pancreatic ductal adenocarcinoma.

The present invention may be used to treat a neoplastic disease, such as solid or non-solid cancers. As used herein, "treatment" encompasses the prevention, reduction, control and/or inhibition of a neoplastic disease. Such diseases include a sarcoma, carcinoma, adenocarcinoma, melanoma, myeloma, blastoma, glioma, lymphoma or leukemia. Exemplary cancers include, for example, sarcoma, adenocarcinoma, melanoma, neural (blastoma, glioma), mesothelioma and reticuloendothelial, lymphatic or haematopoietic neoplastic disorders (e.g., myeloma, lymphoma or leukemia). In some aspects, a neoplasm, tumour or cancer includes a lung adenocarcinoma, lung carcinoma, diffuse or interstitial gastric carcinoma, colon adenocarcinoma, prostate adenocarcinoma, esophagus carcinoma, breast carcinoma, pancreas adenocarcinoma, ovarian adenocarcinoma, adenocarcinoma of the adrenal gland, adenocarcinoma of the endometrium or uterine adenocarcinoma. Neoplasia, tumours and cancers include benign, malignant, metastatic and non-metastatic types, and include any stage (I, II, III, IV or V) or grade (G1, G2, G3, etc.) of neoplasia, tumour, or cancer, or a neoplasia, tumour, cancer or metastasis that is progressing, worsening, stabilized or in remission. The cancer at the onset of practising the invention is clinically defined as being Stage I, Stage II or Stage III or Stage IV or Stage V.

Cancers that may be treated according to the invention include but are not limited to; bladder, blood, bone, bone marrow, brain, breast, colon, esophagus, gastrointestines, gum, head, kidney, liver, lung, nasopharynx, neck, ovary, prostate, skin, stomach, testis, tongue, or uterus. Preferably, the cancer is selected from prostate cancer, liver cancer, renal cancer, lung cancer, breast cancer, colorectal cancer, pancreatic cancer, brain cancer, hepatocellular cancer, lymphoma, leukaemia, gastric cancer, cervical cancer, ovarian cancer, thyroid cancer, melanoma, head and neck cancer, skin cancer and soft tissue sarcoma and/or other forms of carcinoma. The tumour may be metastatic or a malignant tumour, most preferably metastatic. More preferably, the cancer is pancreatic, colorectal, prostate, ovarian cancer, most preferably the cancer is pancreatic, most preferably the cancer is metastatic pancreatic cancer.

The non-pathogenic non-viable *Mycobacterium* of the invention may be administered via the parenteral, oral, sublingual, nasal or pulmonary route. Further preferably, the parenteral route is selected from subcutaneous, intradermal, subdermal, intraperitoneal, intravenous, peritumoral, perilesional, intralesional or intratumoral, and combinations thereof. Suitably, intratumoral administration may be sequentially followed by intradermal administration.

Alternatively, the pathogenic non-viable *Mycobacterium* is *M. obuense*, the subject is simultaneously, separately or sequentially administered a nucleoside metabolic inhibitor, preferably gemcitabine, and is further administered one or more checkpoint inhibitors, preferably pembrolizumab, wherein the subject is classified as having a performance status of 2, 3 or 4 according to the ECOG Scale, or classified as not being sufficiently fit to tolerate two or more chemotherapy regimens, e.g. PS 1 minus.

According to another aspect of the invention, the performance status of the subject stays the same or improves during and/or after said treatment, reduction, inhibition or control of said cancer. In further embodiments, uses or methods according to invention results in: (1), reducing or inhibiting formation or establishment of metastases arising from a primary tumour or cancer to one or more other sites, locations or regions distinct from the primary tumour or cancer; (2) reducing or inhibiting growth or proliferation of a metastasis at one or more other sites, locations or regions distinct from the primary tumour or cancer after a metastasis has formed or has been established, (3) reducing or inhibiting formation or establishment of additional metastasis after the metastasis has been formed or established, (4) prolonged overall survival, (5) prolonged progression free survival, (6) disease stabilisation, (7) increased quality of life, and combinations thereof.

In an embodiment of the invention, there is provided a non-pathogenic, non-viable *Mycobacterium* for use in the treatment, reduction, inhibition or control of cancer in a subject, wherein the subject is clinically classified as having a performance status of 2, 3 or 4 according to the ECOG Scale, or classified as not being sufficiently fit to tolerate two or more chemotherapy regimens, with the potential to elicit potent and durable immune responses with enhanced therapeutic benefit, wherein the use results in: subtotal regression as demonstrated by less than 10% vital tumour cells present in tumour biopsy or resected primary tumour, stable disease (SD), a complete response (CR) or partial response (PR) of the primary tumour; and/or subtotal regression as demonstrated by less than 10% vital tumour cells present in tumour biopsy or resected metastatic tumour, stable disease (SD) or complete response (CR) of one or more non-target tumours, as assessed by Immune Related Response Criteria (irRC), iRECIST, REIST 1.1 or irRECIST, preferably as assessed following surgery and/or end of therapy and/or following administration of 1, 2, 3, 4, 5 or 6 or more doses of said non-pathogenic non-viable *Mycobacterium*.

In an embodiment of the invention, there is provided a non-pathogenic, non-viable *Mycobacterium* for use in the treatment, reduction, inhibition or control of cancer in a subject, or a method according the invention disclosed herein, wherein the treatment, reduction, inhibition or control of said cancer results in a clinically relevant improvement in one or more markers of disease status and progression selected from one or more of the following: (i): overall survival, (ii): progression-free survival, (iii): disease free survival, (iv): overall response rate, (v): reduction in primary tumour size and/or metastatic disease, (vi): circulating levels of tumour antigens such as carbohydrate antigen 19.9 (CA19.9) and carcinoembryonic antigen (CEA) or others depending on tumour, (vii) nutritional status (weight, appetite, serum albumin), (viii): pain control or analgesic use, (ix) CRP/albumin ratio, (x) improved Quality of Life, (xi) maintenance of lean body mass, (xii) reduced potential or incidence of cachexia, or (xiii) a reduction or elimination in ctDNA, preferably as assessed following surgery and/or end of therapy and/or following administration of 1, 2, 3, 4, 5 or 6 or more doses of said non-pathogenic non-viable *Mycobacterium*.

In a further embodiment of the invention, there is provided a non-pathogenic, non-viable *Mycobacterium* for use in the treatment, reduction, inhibition or control of cancer in a subject, or a method according the invention disclosed herein, which results in: prolonged progression free survival according to RECIST 1.1 or iRECIST; prolonged Duration of Response (DoR) according to RECIST 1.1 or iRECIST; or an accelerated Time to Response (TtR) according to RECIST 1.1 or iRECIST, preferably as assessed following surgery and/or end of therapy and/or following administration of 1, 2, 3, 4, 5 or 6 or more doses of said non-pathogenic non-viable *Mycobacterium*.

In an embodiment of the invention, administration of the checkpoint inhibitor, in combination therapy with the, non-pathogenic non-viable *Mycobacterium*, provides a detectable or measurable improvement or overall response according to the irRC (as derived from time-point response assessments and based on tumour burden), including one of more of the following: (i) irCR—complete disappearance of all lesions, whether measurable or not, and no new lesions (confirmation by a repeat, consecutive assessment no less than 4 weeks from the date first documented), (ii) irPR—decrease in tumour burden >50% relative to baseline (confirmed by a consecutive assessment at least 4 weeks after first documentation). Preferably, the checkpoint inhibitor employed is directed against CTLA-4, PD-1, or PD-L1, and combinations thereof. In some embodiments of the invention, the treatment, reduction, inhibition or control of the early-stage cancer further comprises administration of one or more additional anticancer treatments or agents.

The one or more therapeutic agents or modalities may be selected from: adoptive cell therapy, surgical therapy, chemotherapy, radiation therapy, hormonal therapy, checkpoint inhibitor therapy, small molecule therapy such as metformin, receptor kinase inhibitor therapy such as tyrosine kinase inhibitor therapy, hyperthermia treatment, phototherapy, radiofrequency ablation therapy (RFA), anti-angiogenic therapy, cytokine therapy, cryotherapy, biological therapy, HDAC inhibitor e.g. OKI-179, BRAF inhibitor, MEK inhibitor, EGFR inhibitor, VEGF inhibitor, P13K delta inhibitor, PARP inhibitor, mTOR inhibitor, hypomethylating agents, oncolytic virus, TLR agonist including TLR2, 3, 4, 7, 8 or 9 agonists, such as rintatolimod or TLR 5 agonists such as MRx0518 (4D Pharma), STING agonists (including MIW815 and SYNB1891), mifamurtide and cancer vaccines such as GVAX or CIMAvax, and combinations thereof.

In another embodiment of the invention, the one or more therapeutic agents or modalities results in immunogenic cell death therapy, as described in WO2013/07998. This therapy results in the induction of tumour immunogenic cell death, including apoptosis (type 1), autophagy (type 2) and necrosis (type 3), whereupon there is a release of tumour antigens that are able to both induce immune responses, including activation of cytotoxic CD8+ T cells and NK cells and to act as targets, including rendering antigens accessible to Dendritic Cells. The immunogenic cell death therapy may be carried out at sub-optimal levels, i.e. non-curative therapy such that it is not intended to fully remove or eradicate the tumour, but nevertheless results in some tumour cells or tissue becoming necrotic.

The skilled person will appreciate the extent of therapy required in order to achieve this, depending on the technique used, age of the patient, status of the disease and particularly size and location of tumour or metastases Particularly preferred treatments include: microwave irradiation, targeted radiotherapy such as stereotactic ablative radiation (SABR), embolisation, cryotherapy, ultrasound, high intensity focused ultrasound, cyberknife, hyperthermia, radiofrequency ablation, cryoablation, electrotome heating, hot water injection, alcohol injection, embolization, radiation exposure, photodynamic therapy, laser beam irradiation, and combinations thereof.

In a further embodiment of the invention, the TLR agonists include MRx0518 (4D Pharma), mifamurtide (Mepact), Krestin (PSK), IMO-2125 (tilsotolimod), CMP-001, MGN-1703 (lefitolimod), entolimod, rintatolimod (Ampligen), SD-101, GS-9620, imiquimod, resiquimod, MED14736, poly I:C, CPG7909, DSP-0509, VTX-2337 (motolimod), MED19197, NKTR-262, G100 or PF-3512676 and combinations thereof.

In a further embodiment of the invention, the chemotherapy comprises cytotoxic chemotherapeutic agents selected from: bevacizumab, cyclophosphamide, methotrexate, 5-fluorouracil, doxorubicin, mustine, vincristine, procarbazine, prednisolone, bleomycin, vinblastine, dacarbazine, etoposide, cisplatin, epirubicin, capecitabine, leucovorin, folinic acid, carboplatin, oxaliplatin, gemcitabine, FOLFIRINOX, FOLFOX, mFOLFIRINOX, NALIRIFOX, paclitaxel, nab-paclitaxel, pemetrexed, irinotecan, temozolomide and combinations thereof, wherein said one or more agents is administered intratumorally, intraarterially, intravenously, intravascularly, intrapleuraly, intraperitoneally, intratracheally, intranasally, pulmonarily, intrathecally, intramuscularly, endoscopically, intralesionally, percutaneously, subcutaneously, regionally, stereotactically, orally or by direct injection or perfusion, optionally wherein the human patient demonstrated a partial response or stable disease.

In a further embodiment of the invention, the chemotherapy comprises previous or concurrent FOLFIRINOX, FOLFOX, FOLFIRI, mFOLFIRINOX, NALIRIFOX or similar regimens, further wherein said regimens require modification of the dosage and/or timing and/or duration of one or more components provided under such regimens, as would be known to the skilled person for treating said human patient.

In a further embodiment of the invention, the combination is suitable for treatment of pMMR-MSI-Low CRC tumours, i.e. mismatch repair proficient and microsatellite instability low tumours, such as combinations with or without FOLFIRINOX, FOLFOX, FOLFIRI, mFOLFIRINOX, NALIRIFOX or similar regimens, and checkpoint inhibitors such as pembrolizumab and/or atezolizumab, or durvalumab and/or tremelimumab, in combination with a non-pathogenic non-viable *Mycobacterium*. Other combinations include atezolizumab plus bevacizumab together with a non-pathogenic non-viable *Mycobacterium*.

In a further embodiment of the invention, the combination is suitable for treatment of pMMR-MSI-Low tumours, wherein the non-pathogenic, non-viable *Mycobacterium* is administered in combination with one or more of the following combinations: RFA and/or EBRT and/or pembrolizumab; RFA and/or durvalumab and/or tremelimumab, atezolizumab and/or bevacizumab and/or FOLFIRNOX, FOLFOX, FOLFIRI, mFOLFIRINOX, NALIRIFOX or similar regimens; atezolizumab and cobimetinib; nivolumab+ipilimumab+cobimetinib; atezolizumab+cobimetinib+bevacizumab; Atezolizumab+CEA-BTC antibody; Pembrolizumab+indoximod; nivolumab+epacadostat; durvalumab+pexidartinib.

In a further embodiment of the invention, the combination comprises either radiofrequency ablation (RFA) or external beam radiation therapy (EBRT) in patients with for example, CRC, together with checkpoint inhibitors such as pembrolizumab and/or atezolizumab, or durvalumab and/or tremelimumab, in combination with a non-pathogenic non-viable *Mycobacterium.*

In a further embodiment of the invention, the adjuvant, neoadjuvant or peri-adjuvant therapy disclosed herein is applied to patients with stage III dM MR and/or MSI-High colorectal cancer, or colon cancer or rectal cancer, wherein said patient presents with an ECOG Performance Status of 0 (PS0), 1 (PS1) or PS1-, or 2 (PS2).

In a further embodiment of the invention, the adjuvant, neoadjuvant or peri-adjuvant therapy disclosed herein, is applied to patients who present with an ECOG Performance Status of 0 (PS0), 1 (PS1) or PS1- or 2 (PS2) and wherein said Performance Status value is the same or improved when assessed post-surgery or at the end of therapy.

In a further embodiment of the invention, the adjuvant, neoadjuvant or peri-adjuvant therapy disclosed herein is applied to patients with stage III pMMR/MSI-Low colorectal cancer, or colon cancer or rectal cancer i.e. mismatch repair proficient and microsatellite instability low tumours in patients with colorectal cancer, or colon cancer or rectal cancer, wherein said patient presents with an ECOG Performance Status of 0 (PS0), 1 (PS1) or PS1- or 2 (PS2).

In some preferred embodiments, the one or more additional anticancer treatments or agents may include one or more checkpoint inhibitors selected from: ipilimumab, nivolumab, pembrolizumab, azetolizumab, BI 754091 (anti-PD-1), bavituximab (an IgG3 mab against PS), bintrafusp alfa, dostarlimab, durvalumab, tremelimumab, spartalizumab, avelumab, sintilimab, toripalimab, prolgolimab, tislelizumab, camrelizumab, MGA012, MGD013 (now known as tebotelimab), KN046 (PD-L1/CTLA-4 bispecific antibody), MGD019, enoblituzumab, MGD009, MGC018, MED10680, miptenalimab (BI 754111, an anti-LAG-3), nimotuzumab PDR001, FAZ053, TSR022, MBG453, relatlimab (BMS986016), LAG525 (IMP701), IMP321 (Eftilagimod alpha), REGN2810 (cemiplimab), REGN3767, pexidartinib (PLX3397), LY3022855, FPA008, BLZ945, GDC0919, epacadostat, emactuzumab (RG1755 targeting CSF-1R), FPA150, indoximid, BMS986205, CPI-444, MED19447, PBF509, FS118 (bispecific for LAG-3 and PD-L1), lirilumab, Sym023, TSR-022, A2Ar inhibitors (e.g. E05100850, AB928), NKG2A inhibitors such as monalizumab, and combinations thereof, optionally administered in a sub-therapeutic amount and/or duration.

In other embodiments of the invention, the tumour and/or metastases may be surgically removed via resection, which results in a tumour margin as defined according to the AJCC 8<sup>th</sup> Edition, such as an R0 resection margin, where no cancer cells are seen microscopically at the primary tumour site; or R1, where cancer cells are present microscopically at the primary tumour site; or, R2, where macroscopic residual tumour is found at the primary cancer site and/or regional lymph nodes.

In a further embodiment, a combination according to the invention is administered within 1, 2, 5, 10, 20, 30, 40, 50, 60 or 70 days after tumour resection, wherein said tumour resection is suitably an R0, R1 or R2 resection, preferably R0 and optionally continued to be administered no later than 70 days after said resection.

In a further embodiment, within 70 days post tumour resection, the *Mycobacterium* may be initially administered intradermally, at an initial dose of 1.0 mg at 14±2 days prior to the administration of the first infusion of atezolizumab, followed by administration of atezolizumab intravenously at a dose of 840 mg every 2 weeks, for a period of 12 months following said tumour resection, combined with administration of the *Mycobacterium* at a dose of 0.5 or 1.0 mg every 2 weeks for one month, followed by a dose of 0.5 or 1.0 mg *Mycobacterium* every 4 weeks for 11 months, on the same or different day as said atezolizumab infusion, preferably wherein said *Mycobacterium* is *M. obuense* NCTC 13365.

In a further embodiment, atezolizumab may be administered intravenously at a dose of 1200 mg 28 days and 7 days prior to tumour resection, with administration of the *Mycobacterium*, administered intradermally, at a dose of 1.0 mg 35 days prior to tumour resection, followed by administration of the *Mycobacterium*, at a dose of 0.5 or 1.0 mg 21 days and 5 days prior to tumour resection, preferably wherein said *Mycobacterium* is *M. obuense* NCTC 13365.

In a further embodiment, the invention comprises a neoadjuvant, adjuvant or peri-adjuvant regimen in a human subject, wherein said non-viable, non-pathogenic *Mycobacterium* and one or more additional anticancer treatments or agents are administered, optionally at the same or different time, via the same or different route of administration, and where the human subject demonstrates a pathological complete or particle/subtotal response or tumour regression at 5 weeks or later post-surgery or end of therapy, and/or an increased disease-free survival (DFS) or Overall Survival (OS) at 1, 2, 3 or 5 years or later, post-surgery or end of therapy, and/or an improved quality of life (assessed by EORTC QLQ-C30 and PRO-CTCAE questionnaires after 4, 12 weeks, and then quarterly), and/or no detectable ctDNA at 12 months or later, post-surgery or end of therapy, preferably wherein said *Mycobacterium* is *M. obuense* NCTC 13365.

Circulating tumor DNA ("ctDNA") is found in the bloodstream and refers to DNA that comes from cancerous cells and tumours. Measurement of ctDNA has emerged as a promising blood-based biomarker for monitoring disease status of patients with advanced cancers. The presence of ctDNA in the blood is a result of biological processes, namely tumour cell apoptosis and/or necrosis, and can be used to monitor different cancers by targeting cancer-specific mutation.

An invention method may not take effect immediately. For example, treatment may be followed by an increase in the neoplasia, tumour or cancer cell numbers or mass, but over time eventual stabilization or reduction in tumour cell mass, size or numbers of cells in a given subject may subsequently occur. Additional adverse symptoms and complications associated with neoplasia, tumour, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of an adverse symptom or complication associated with or caused by a cellular hyperproliferative disorder, an improvement in the subject's quality of life and/or well-being, such as increased energy, appetite, psychological well-being, are all particular non-limiting examples of therapeutic benefit, including a reduced potential or incidence of cachexia.

Treatment with non-pathogenic, non-viable *M. vaccae* and/or *M. obuense* gives rise to more complex immunity including not only the development of innate immunity and type-1 immunity, but also immunoregulation which more efficiently restores appropriate immune functions. In another preferred embodiment, the checkpoint inhibitor is administered in a sub-therapeutic amount and/or duration.

In another embodiment, the checkpoint inhibitor is pembrolizumab and said subject or patient has mismatch repair-deficient tumours associated with said cancer and/or exhibits PD-L1 expression in at least 1%, 2%, 10%, or 20%, or 30%, or 40%, or 50% or more of tumour cells, as measured using the SP142 immunohistochemistry antibody assay.

In a further embodiment, the inhibitor is an antibody that specifically binds to B7-H3 such as GA271 (an a-B7-H3 humanized monoclonal antibody, Macrogenics, Inc.); or indoleamine-2,3-dioxygenase (IDO) inhibitors such as D-methyl-tryptophan (Lunate).

The term "combination" as used throughout the specification, can encompass the administration of the checkpoint inhibitor simultaneously, separately or sequentially with administration of the, non-pathogenic non-viable *Mycobacterium*. Accordingly, the checkpoint inhibitor and the whole cell, non-pathogenic non-viable *Mycobacterium* may be present in the same or separate pharmaceutical formulations, and administered at the same time or at different times.

Thus, a non-pathogenic non-viable *Mycobacterium* and the checkpoint inhibitor may be provided as separate medicaments for administration at the same time or at different times. Preferably, a non-pathogenic non-viable *Mycobacterium* and checkpoint inhibitor are provided as separate medicaments for administration at different times. When administered separately and at different times, either the non-pathogenic non-viable *Mycobacterium* or checkpoint inhibitor may be administered first; however, it is suitable to administer checkpoint inhibitor followed by the non-pathogenic non-viable *Mycobacterium*. In addition, both can be administered on the same day or at different days, and they can be administered using the same schedule or at different schedules during the treatment cycle. In an embodiment of the invention, a treatment cycle consists of the administration of a non-pathogenic non-viable *Mycobacterium* daily, weekly fortnightly or monthly, simultaneously with checkpoint inhibitor weekly. Alternatively, the non-pathogenic non-viable *Mycobacterium* is administered before and/or after the administration of the checkpoint inhibitor. In another embodiment of the invention, the non-pathogenic non-viable *Mycobacterium* is administered to the patient before and after administration of a checkpoint inhibitor. That is, in one embodiment, the non-pathogenic non-viable *Mycobacterium* is administered to the patient before and after said checkpoint inhibitor. Dose delays and/or dose reductions and schedule adjustments are performed as needed depending on individual patient tolerance to treatments. Alternatively, the administration of checkpoint inhibitor may be performed simultaneously with the administration of the effective amounts of the non-pathogenic non-viable *Mycobacterium*.

In an embodiment of the invention, the effective amount of the non-pathogenic non-viable *Mycobacterium* may be administered as a single dose. Alternatively, the effective amount of the non-pathogenic non-viable *Mycobacterium* may be administered in multiple (repeat) doses, for example two or more, three or more, four or more, five or more, ten or more, or twenty or more repeat doses. The non-pathogenic non-viable *Mycobacterium* may be administered between about 4 weeks and about 1 day prior to the checkpoint inhibitor such as between about 4 weeks and 1 week, or about between 3 weeks and 1 week, or about between 3 weeks and 2 weeks. Administration may be presented in single or multiple doses.

In a further embodiment, the invention provides a non-viable *Mycobacterium* which mediates any combination of at least one of the following immunostimulatory effects on immunity, preferably wherein said *Mycobacterium* is *M. obuense* NCTC 13365: (i) increasing immune response, (ii) increasing T cell activation, (iii) increasing cytotoxic T cell activity, (iv) increasing NK cell activity, (v) increasing Th17 activity, (vi) alleviating T-cell suppression, (vii) increasing pro-inflammatory cytokine secretion, (viii) increasing IL-2 secretion; (ix) increasing interferon-γ production by T-cells, (x) increasing Th1 response, (xi) decreasing Th2 response, (xii) decreasing or eliminating at least one of regulatory T cells (Tregs), myeloid derived suppressor cells (MDSCs), iMCs, mesenchymal stromal cells, TIE2-expressing monocytes, (xiii) reducing regulatory cell activity and/or the activity of one or more of myeloid derived suppressor cells (MDSCs), iMCs, mesenchymal stromal cells, TIE2-expressing monocytes, (xiv) decreasing or eliminating M2 macrophages, (xv) reducing M2 macrophage pro-tumorigenic activity, (xvi) decreases or eliminates N2 neutrophils, (xvii) reduces N2 neutrophils pro-tumorigenic activity, (xviii) reducing inhibition of T cell activation, (xix) reducing inhibition of CTL activation, (xx) reducing inhibition of NK cell activation, (xxi) reversing T cell exhaustion, (xxii) increasing T cell response, (xxiii) increasing activity of cytotoxic cells, (xxiv) stimulating antigen-specific memory responses, (xxv) eliciting apoptosis or lysis of cancer cells, (xxvi) stimulating cytotoxic or cytostatic effect on cancer cells, (xxvii) inducing direct killing of cancer cells, and/or (xxviii) inducing complement dependent cytotoxicity and/or (xxix) inducing antibody dependent cell-mediated cytotoxicity.

In one embodiment of the present invention, the non-pathogenic non-viable *Mycobacterium* may be in the form of a medicament administered to the patient in a dosage form. A container according to the invention in certain instances may be a vial, an ampoule, a syringe, capsule, tablet or a tube. In some cases, the mycobacteria may be lyophilized and formulated for resuspension prior to administration. However, in other cases, the mycobacteria are suspended in a volume of a pharmaceutically acceptable liquid. In some embodiments, there is provided a container comprising a single unit dose of mycobacteria suspended in pharmaceutically acceptable carrier wherein the unit dose comprises about $1 \times 10^6$ to about $1 \times 10^{10}$ organisms. In some embodiments the liquid comprising suspended mycobacteria is provided in a volume of between about 0.1 ml and 10 ml, or between about 0.3 ml and 2 ml or between about 0.5 ml and 2 ml. The foregoing compositions provide ideal units for immunotherapeutic applications described herein.

Embodiments discussed in the context of a methods and/or composition of the invention may be employed with respect to any other method or composition described herein. Thus, an embodiment pertaining to one method or composition may be applied to other methods and compositions of the invention as well. In some cases, whole cell non-pathogenic non-viable Mycobacteria are administered to specific sites on or in a subject. For example, the mycobacterial compositions according to the invention, such as those comprising *M. obuense* in particular, may be administered adjacent to tumours or adjacent to lymph nodes, such as those that drain tissue surrounding a tumour. Thus, in certain instances sites administration of mycobacterial composition may be near the posterior cervical, tonsillar, axillary, inguinal, anterior cervical, sub-mandibular, sub mental or superclavicular lymph nodes. The whole cell, non-pathogenic heat-killed *Mycobacterium* may be administered for the length of time the cancer or tumour(s) is present in a patient or until such time the cancer has regressed or stabilized. The whole cell, non-pathogenic non-viable

*Mycobacterium* may also be continued to be administered to the patients once the cancer or tumour has regressed or stabilised.

Mycobacterial compositions according to the invention will comprise an effective amount of mycobacteria typically dispersed in a pharmaceutically acceptable carrier. The phrases "pharmaceutically or pharmacologically acceptable" refers to molecular entities and compositions that do not produce an adverse, allergic or other untoward reaction when administered to an animal, such as, for example, a human, as appropriate. The preparation of a pharmaceutical composition that contains mycobacteria will be known to those of skill in the art. Moreover, for animal (e.g., human) administration, it will be understood that preparations should meet sterility, pyrogenicity, general safety and purity standards. A specific example of a pharmacologically acceptable carrier as described herein is borate buffer or sterile saline solution (0.9% NaCl). As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavouring agents, dyes, such like materials and combinations thereof, as would be known to one of ordinary skill in the art.

In another embodiment, the whole cell, non-pathogenic non-viable *Mycobacterium* is administered via a parenteral route selected from subcutaneous, intradermal, subdermal, intraperitoneal, intravenous and intravesicular injection. Intradermal injection enables delivery of an entire proportion of the mycobacterial composition to a layer of the dermis that is accessible to immune surveillance and thus capable of electing an anti-cancer immune response and promoting immune cell proliferation at local lymph nodes. In some embodiments of the invention mycobacterial compositions are administered by direct intradermal injection, it is also contemplated that other methods of administration may be used in some case. Thus in certain instances, the whole cell, non-pathogenic non-viable *Mycobacterium* of the present invention can be administered by injection, infusion, continuous infusion, intravenously, intradermally, intraarterially, intraperitonealy, intralesionally, intravitreally, intravaginally, intrarectally, topically, intratumourally, intramuscularly, intraperitoneally, subcutaneously, subconjunctival, intravesicularlly, mucosally, intrapericardially, intraumbilically, intraocularally, orally, intracranially, intraarticularly, intraprostaticaly, intrapleural, intratracheally, intranasally, intranodally, topically, locally, inhalation (e.g. aerosol inhalation), perilesionally, peritumorally, percutaneously, regionally, stereotactically, orally or by direct injection or perfusion via a catheter, via a lavage, or by other method or any combination of the forgoing as would be known to one of ordinary skill in the art.

A further embodiment of the invention is a method of treating, reducing, inhibiting or controlling cancer in a subject, wherein said method comprises simultaneously, separately or sequentially administering to the subject (i) one or more therapeutic agents and/or cancer treatments and (ii) a non-pathogenic non-viable *Mycobacterium*, wherein said method results in enhanced therapeutic efficacy relative to administration of one or more therapeutic agents and/or cancer treatments alone, and wherein the subject is clinically classified as having a performance status of 1-, 2, 3 or 4 according to the ECOG Scale, or as not being sufficiently fit to tolerate two or more chemotherapeutic regimens. Preferably, the subject is classified as having a performance status of 2 (PS 2).

In other aspects of the invention, the non-pathogenic non-viable *Mycobacterium* used in the method is *M. vaccae, M. parafortuitum, M. aurum, M. indicus pranii* and combinations thereof, most preferably *M. obuense*. Preferably, the non-pathogenic non-viable *Mycobacterium* is heat-killed. Preferably, the non-pathogenic non-viable *Mycobacterium* is the rough variant. Further preferably, the non-viable *Mycobacterium* is administered to the subject as a first line treatment, optionally simultaneously, separately or sequentially with administration of one or more therapeutic agents or modalities.

In some aspects of the method, the subject or patient receives one or more cytotoxic chemotherapeutic agents, such as FOLFIRINOX. The subject may also be administered a nucleoside metabolic inhibitor, preferably gemcitabine. Preferably, the subject may be administered a microtubule inhibitor, most preferably nab-paclitaxel, in combination with gemcitabine. In some aspects of the method, the subject may also be administered targeted radiotherapy, such as stereotactic body radiation therapy (e.g. Cyberknife®).

In some aspects of the use or method, the human patient receives radiotherapy for palliative or pain relief purposes. Alternatively, the human patient may be administered said radiotherapies with a therapeutic or/curative intent.

In some embodiments, the checkpoint inhibitor therapy may further comprise co-stimulatory checkpoint therapy, directed against any one of the following combinations: CTLA-4 and CD40, CTLA-4 and OX40, CTLA-4 and IDO, OX-40 and PD-L1, PD-1 and OX-40, CD27 and PD-L1, PD-1 and CD137, PD-L1 and CD137, OX-40 and CD137, CTLA-4 and IDO, PD-1 and IDO, PD-L1 and IDO, PD! And A2AR, PD-L1 and A2AR, PD1 and GITR, PD-L1 and GITR, PD1 and ICOS, PD-L1 and ICOS, PD1 and CD27, PD-L1 and CD27, PD1 and CD122, PD-L1 and CD122, PD1 and CSF1R, PD-L1 and CSF1R, and other such suitable combinations.

Suitable specific combinations include: Avelumab+utomilumab, Nivolumab+urelumab, Pembrolizumab+utomilumab, Atezolimumab+MOXR0916±bevacizumab, Avelumab+PF-04518600, Durvalumab+MED10562, Pembrolizumab+GSK3174998, Tremelimumab+durvalumab+MED16469, Tremelimumab+MED10562, Utomilumab+PF-04518600, Atezolimumab+RO7009789, Tremelimumab+CP870893, Nivolumab+BMS986156, PDR001+GWN323, Nivolumab+JTX-2011, Atezolizumab+GDC0919, Ipilimumab+epacadostat, Ipilimumab+indoximid, Nivolumab+BMS986205, Pembrolizumab+epacadostat, Atezolizumab+CPI-444, Durvalumab+MED19447, PDR001+PBF509, Nivolumab+varlilumab, Atezolizumab+varlilumab, Nivolumab+NKTR-214, Durvalumab+Pexidartinib (PLX3397), Durvalumab+LY3022855, Nivolumab+FPA008, Pembrolizumab+Pexidartinib, PDR001+BLZ945, Tremelimumab+LY3022855.

In a further embodiment, the checkpoint inhibitor therapy comprises administration of a blocking agent, wherein said blocking agent is an antibody selected from the group consisting of: AMP-224 (Amplimmune, Inc), BMS-986016 or MGA-271, and combinations thereof. AMP-224, also known as B7-DC1g, is a PD-L2-Fc fusion soluble receptor described in WO2010/027827 and WO2011/066342.

In a further embodiment, the checkpoint inhibitor therapy comprises administration of a blocking agent wherein said blocking agent is an antibody that specifically binds to B7-H3 such as enoblituzumab, an engineered Fc humanized IgG1 monoclonal antibody against B7-H3 with potent anti-tumor activity (Macrogenics, Inc.), or MGD009, a B7-H3 dual affinity re-targeting (DART) protein that bind both CD3 on T cells and B7-H3 on the target cell which has been found to recruit T cells to the tumor site and promote tumour eradication, or MGD009 is a humanized DART protein. MGC018 is anti-B7-H3 antibody drug conjugate (ADC) with a duocarmycin payload and cleavable peptide linker.

In some embodiments, the checkpoint inhibitor therapy comprises administration of an anti-B7-H3-binding protein selected from the group consisting of DS-5573 (Daiichi Sankyo, Inc.), enoblituzumab (MacroGenics, Inc.), and omburtamab [8H9] (Y-mabs Therapeutics, Inc), an antibody against B7-H3 labeled with radioactive iodine (I-131).

In certain embodiments, the co-stimulatory checkpoint therapy upregulates the cellular immune system, wherein said co-stimulatory checkpoint therapy comprises adminis-tration of a binding agent, selected from a cell, protein, peptide, antibody or antigen binding fragment thereof, directed against CD27, OX40, GITR, or CD137, and com-binations thereof, such as CD137 agonists including without limitation BMS-663513 (urelumab, an anti-CD137 human-ized monoclonal antibody agonist, Bristol-Myers Squibb); agonists to CD40, such as CP-870,893 (a-CD40 humanized monoclonal antibody, Pfizer); OX40 (CD 134) agonists (e.g. anti-OX40 humanized monoclonal antibodies, AgonOx and those described in U.S. Pat. No. 7,959,925), and Astra Zeneca's MED10562, a humanised OX40 agonist; MED16469, murine OX4 agonist; and MED16383, an OX40 agonist; or agonists to CD27 such as CDX-1127 (a-CD27 humanized monoclonal antibody, Celldex). Suit-able anti-GITR antibodies include TRX518 (Tolerx), MK-1248 (Merck), CK-302 and suitable anti-4-1BB anti-bodies for use in the invention include PF-5082566 (Pfizer).

In one embodiment of the invention, the subject is further administered one or more nutraceuticals selected from amino acids, antioxidants, fats, vitamins, trace elements, minerals, micronutrients, plant extracts, phytochemicals, fibres, prebiotics, probiotics, and/or a combination thereof, preferably vitamin D, vitamin C and/or zinc. Vitamin D may have a pleiotropic effect in immune cells, including macro-phages, and an immunomodulatory role of vitamin D in various immune cells and diseases has been demonstrated. Accordingly, suitable presentations of vitamin D may include oral or injected formulations of paricalcitol e.g. 1 mcg orally; cholecalciferol, 60,000 IU orally per week or single injections of 300,000 Us; or 300,000 IUs of ergocal-ciferol injected. 5-hydroxyvitamin D levels may be moni-tored frequently depending on local clinical practice, e.g. every 12 weeks, with supplementation of vitamin D as required, in combination therapy with the non-pathogenic non-viable *Mycobacterium* of the invention is envisaged. Supplementation with protidic (high protein content) liquids are also envisaged, e.g. Ensure.

Neoplasia, tumours and cancers include benign, malig-nant, metastatic and non-metastatic types, and include any stage (I, II, Ill, IV or V) or grade (G1, G2, G3, etc.) of neoplasia, tumour, or cancer, or a neoplasia, tumour, cancer or metastasis that is progressing, worsening, stabilized or in remission.

In a further embodiment, the cancer is defined as under the TNM classification system, in particular by a T of for example, T1-T4, and optionally an M of M0, whilst N can be any classification, such as N0, N1 or N2. Alternatively, said cancer is clinically defined as being Stage I, Stage II or Stage III. In other words, the cancer may be early-stage and/or is defined by a recorded size and growth of any size.

In a further preferred embodiment or method of the invention, the patient does not present with metastases in any organs distant to the primary tumour but may present with metastases in one or more lymph nodes near to the primary neoplasia or tumour, and/or may present with metastases in one or more nearby organs. Alternatively, said patient does not present with any macroscopic residual disease following tumour resection surgery, as demonstrated by an R2 resection status.

In a further preferred embodiment or method of the invention, the human patient is clinically defined as non-metastatic. Alternatively, the human patient presents with metabolically active regional nodes (via PET scan) and is thus deemed to be metastatic, optionally where said human patient does not present with liver or lungs metastases. Or, some patients may present with peritoneal metastases but no liver or lung metastases, and permutations thereof.

Cancers that may be treated according to the invention include but are not limited to; bladder, blood, bone, bone marrow, brain, breast, colon, esophagus, gastrointestines, gum, head, kidney, liver, lung, nasopharynx, neck, ovary, prostate, skin, stomach, testis, tongue, or uterus.

In addition, the cancer may specifically be of the follow-ing histological type, though it is not limited to the follow-ing: neoplasm, malignant carcinoma; carcinoma, undiffer-entiated; giant and spindle cell carcinoma; small cell carcinoma; papillary carcinoma; squamous cell carcinoma; lymphoepithelial carcinoma; basal cell carcinoma; piloma-trix carcinoma; transitional cell carcinoma; papillary transi-tional cell carcinoma; adenocarcinoma; gastrinoma, malig-nant cholangiocarcinoma; hepatocellular carcinoma; combined hepatocellular carcinoma and cholangiocarci-noma; trabecular adenocarcinoma; adenoid cystic carci-noma; adenocarcinoma in adenomatous polyp; adenocarci-noma, familial polyposis coli; solid carcinoma; carcinoid tumour, malignant bronchiolo-alveolar adenocarcinoma; papillary adenocarcinoma; chromophobe carcinoma; aci-dophil carcinoma; oxyphilic adenocarcinoma; basophil car-cinoma; clear cell adenocarcinoma; granular cell carcinoma; follicular adenocarcinoma; papillary and follicular adeno-carcinoma; nonencapsulating sclerosing carcinoma; adrenal cortical carcinoma; endometroid carcinoma; skin appendage carcinoma; apocrine adenocarcinoma; sebaceous adenocar-cinoma; ceruminous adenocarcinoma; mucoepidermoid car-cinoma; cystadenocarcinoma; papillary cystadenocarci-noma; papillary serous cystadenocarcinoma; mucinous cystadenocarcinoma; mucinous adenocarcinoma; signet ring cell carcinoma; infiltrating duct carcinoma; medullary car-cinoma; lobular carcinoma; inflammatory carcinoma; Pag-et's disease, mammary; acinar cell carcinoma; adenosqua-mous carcinoma; adenocarcinoma with squamous metaplasia; thymoma, malignant ovarian stromal tumour, malignant thecoma, malignant granulosa cell tumour, malig-nant androblastoma, malignant Sertoli cell carcinoma; Ley-dig cell tumour, malignant lipid cell tumour, malignant paraganglioma, malignant extra-mammary paraganglioma, malignant pheochromocytoma; glomangiosarcoma; malig-nant melanoma; amelanotic melanoma; superficial spread-ing melanoma; malignant melanoma in giant pigmented nevus; metastatic melanoma, Lentigo Maligna, Lentigo Maligna Melanoma, cutaneous squamous cell carcinoma, Nodular Melanoma, Acral Lentiginous Melanoma, desmo-plastic Melanoma, epithelioid cell melanoma; blue nevus, malignant sarcoma; fibrosarcoma; fibrous histiocytoma, malignant myxosarcoma; liposarcoma, leiomyosarcoma;

rhabdomyosarcoma; embryonal rhabdomyosarcoma; alveolar rhabdomyosarcoma; undifferentiated pleomorphic sarcoma; stromal sarcoma; mixed tumour; Mullerian mixed tumour; nephroblastoma; hepatoblastoma; carcinosarcoma; mesenchymoma, malignant Brenner tumour, malignant phyllodes tumour, malignant synovial sarcoma; mesothelioma, malignant dysgerminoma; embryonal carcinoma; teratoma, malignant; struma ovarii, malignant; choriocarcinoma; mesonephroma, malignant hemangiosarcoma; hemangioendothelioma, malignant Kaposi's sarcoma; hemangiopericytoma, malignant lymphangiosarcoma; osteosarcoma; juxtacortical osteosarcoma; chondrosarcoma; chondroblastoma, malignant mesenchymal chondrosarcoma; giant cell tumour of bone; Ewing's sarcoma; odontogenic tumour, malignant ameloblastic odontosarcoma; ameloblastoma, malignant ameloblastic fibrosarcoma; pinealoma, malignant chordoma; glioma, malignant ependymoma; astrocytoma; protoplasmic astrocytoma; fibrillary astrocytoma; astroblastoma; glioblastoma multiforme; oligodendroglioma; oligodendroblastoma; primitive neuroectodermal; cerebellar sarcoma; ganglioneuroblastoma; neuroblastoma; retinoblastoma; olfactory neurogenic tumour; meningioma, malignant neurofibrosarcoma; neurilemmoma, malignant granular cell tumour, malignant lymphoma; Hodgkin's disease; Hodgkin's paragranuloma; malignant lymphoma, small lymphocytic malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Preferably, the cancer is selected from bladder cancer (including non-muscle invasive bladder cancer), prostate cancer, liver cancer, renal cancer, lung cancer, breast cancer, colorectal cancer, colon cancer, rectal cancer, pancreatic cancer, brain cancer (including glioblastoma), hepatocellular cancer, lymphoma, leukaemia, gastric cancer, cervical cancer, ovarian cancer, thyroid cancer, melanoma, head and neck cancer, skin cancer and soft tissue sarcoma and/or other forms of carcinoma.

The tumour may be metastatic or a malignant tumour, most preferably metastatic. More preferably, the cancer is pancreatic, colorectal, prostate, ovarian cancer, most preferably the cancer is pancreatic, including pancreatic ductal adenocarcinoma (PDAC) or most preferably the cancer is metastatic pancreatic cancer including metastatic pancreatic ductal adenocarcinoma (mPDAC).

In some aspects of the method, the non-pathogenic non-viable *Mycobacterium* may be administered via the parenteral, oral, sublingual, nasal or pulmonary route. Further preferably, the parenteral route is selected from subcutaneous, intradermal, subdermal, intraperitoneal, intravenous, peritumoral, perilesional, intralesional or intratumoral, and combinations thereof. Suitably, intratumoral administration is sequentially followed by intradermal administration.

In another embodiment of the invention, the one or more therapeutic agents or modalities are administrated intratumorally simultaneously, separately or sequentially with the non-pathogenic non-viable *Mycobacterium*. For example, both gemcitabine and the non-pathogenic non-viable whole cell *Mycobacterium* are delivered to the pancreatic site via intra-arterial transit using RenovoCath™ RC120 Catheter (RenovoRx). The RenovoCath™ RC120 Catheter is an endovascular multi-lumen, two-handled catheter designed to isolate variable segments of arteries supplying the target organ using two slideable, compliant balloons. Upon inflation of the proximal occlusion balloon and the distal occlusion balloon the catheter isolates the site to specifically deliver said therapeutic agents. Another suitable combination is intratumoral administration of the non-pathogenic non-viable whole cell *Mycobacterium* together with hafnium oxide nanoparticles, subsequently activated by radiotherapy (NBTXR3, NanoBiotix, Inc.).

Preferably, the non-pathogenic non-viable *Mycobacterium* administered in the method is *M. obuense*, the subject is simultaneously, separately or sequentially administered a nucleoside metabolic inhibitor, preferably gemcitabine, and is further administered one or more checkpoint inhibitors, preferably pembrolizumab, wherein the subject is classified as having a performance status of 2, 3 or 4 according to the ECOG Scale, preferably PS 2, or classified as not being of an age and/or sufficiently fit to tolerate two or more chemotherapy regimens.

In a further embodiment, patients are also administered COVID-19 vaccination at the beginning of the therapy or methods according to the invention, with the second dose delayed by 6 weeks or more depending on the vaccine and in order to ensure there is at least a week between IMM-101, Gem/Nab-P and the next dose. In general, there is a period of 5 to 7 days between COVID-19 vaccination and any chemotherapy.

According to another aspect of the method of the invention, the performance status of the subject stays the same or improves during and/or after said treatment, reduction, inhibition or control of said cancer. In further embodiments, methods of the invention include, one or more of the following: 1) reducing or inhibiting growth, proliferation, mobility or invasiveness of tumour or cancer cells that potentially or do develop metastases, 2) reducing or inhibiting formation or establishment of metastases arising from a primary tumour or cancer to one or more other sites, locations or regions distinct from the primary tumour or cancer; 3) reducing or inhibiting growth or proliferation of a metastasis at one or more other sites, locations or regions distinct from the primary tumour or cancer after a metastasis has formed or has been established, 4) reducing or inhibiting formation or establishment of additional metastasis after the metastasis has been formed or established, 5) prolonged overall survival, 6) prolonged progression free survival, or 7) disease stabilisation.

According to another embodiment of the invention, the performance status of the subject stays the same or improves during and/or after said treatment, reduction, inhibition or control of said cancer, for example, the patient may commence therapy under the invention as PS2 and maintain said score throughout and at the end of the desired therapy or regimens, or the patient may commence therapy under the invention as PS2 and demonstrate an improved performance score throughout and/or at the end of the desired therapy or regimens, such as PS1(−), PS1 or PS0.

In an embodiment of the invention, the combinations and methods disclosed herein result in a clinically relevant improvement in one or more markers of disease status and progression selected from one or more of the following: (i): overall survival, (ii): progression-free survival, (iii): overall response rate, (iv): reduction in metastatic disease, (v): circulating levels of tumour antigens such as carbohydrate antigen 19.9 (CA19.9), carcinoembryonic antigen (CEA), prostate-specific antigen (PSA) or other suitable biomarkers depending on tumour, (vii) nutritional status (weight, appetite, serum albumin), (viii): systemic immune-inflammation index (SII) or systemic inflammation score (SIS), (ix): pain control or analgesic use, or (x): CRP/albumin ratio or prognostic nutritional index (PNI), or neutrophil/lymphocyte ratio (NLR), or (xi) improved Quality of Life, or (xii), a reduction or elimination in ctDNA, preferably as assessed at 12 months post-surgery or end of therapy and/or following administration of 1, 2, 3, 4, 5 or 6 or more doses of said non-pathogenic non-viable *Mycobacterium*.

In some embodiments, the one or more markers of disease status and progression selected from the above list may be measured for monitoring of the treatment, reduction, inhibition or control protocols of the present invention. In some preferred embodiments, the one or more biomarkers may include any one or more of: prostate-specific antigen (PSA); carcinoembryonic antigen (CEA); prognostic nutritional index (PNI); systemic immune-inflammation index (SII); or neutrophil/lymphocyte ratio (NLR) and systemic inflammation score (SIS).

In an embodiment of the invention, the treatment, reduction, inhibition or control of said cancer, which comprises a primary tumour and/or non-target tumours, results in: prolonged progression free survival according to RECIST 1.1 or iRECIST; prolonged Duration of Response (DoR) according to RECIST 1.1 or iRECIST; or an accelerated Time to Response (TtR) according to RECIST 1.1 or iRECIST, preferably as assessed following surgery and/or end of therapy and/or following administration of 1, 2, 3, 4, 5 or 6 or more doses of said non-pathogenic non-viable *Mycobacterium*. Optionally, said responding or non-responding patients are from Europe or outside Europe, such as Eastern, Western or Central Europe, or Indian sub-continent or from Asia.

In an embodiment of the invention, the use, combinations and methods disclosed herein result in a clinically relevant improvement in one or more markers of disease status and progression in patients who demonstrate less than 10% weight loss in the preceding three months prior to commencing therapy.

In a further embodiment of the invention, the use, combinations and methods disclosed herein result in a clinically relevant improvement in one or more markers of disease status and progression in patients who demonstrate not more than 15% weight loss within one month prior to commencing therapy.

In a further embodiment of the invention, the use, combinations and methods disclosed herein result in a clinically relevant improvement in one or more markers of disease status, QoL and progression in patients such as handgrip strength. Handgrip strength may be measured using a digital dynamometer (TTM, Inc., Tokyo, Japan), with the participant standing upright. The patients had shoulder adducted and neutrally rotated, elbows fully extended, forearms and wrists in neutral position, and legs open to shoulder width. Grip strength is maintained or improved at 3 or more months following surgery and/or end of therapy and/or following administration of 1, 2, 3, 4, 5 or 6 or more doses of said non-pathogenic non-viable *Mycobacterium*.

In a further embodiment of the invention, the use, combinations and methods disclosed herein result in a clinically relevant improvement in one or more markers of disease status, QoL and progression in patients such as plasma albumin level. Herein, said plasma albumin level is maintained between 2 and 3 g/dL, preferably at or near 2.8 g/dL, or increased, when measured at 3 or more months following surgery and/or end of therapy and/or following administration of 1, 2, 3, 4, 5 or 6 or more doses of said non-pathogenic non-viable *Mycobacterium*.

In a most preferred embodiment of the invention, is provided a non-pathogenic non-viable *Mycobacterium* for use in the treatment, reduction, inhibition or control of cancer in a subject, wherein the subject is a human patient clinically classified as having a performance status of 1-, 2, 3 or 4 according to the Eastern Cooperative Oncology Group (ECOG) Scale, suitably PS2, herein the subject is a human patient of at least 50, 55, 60, 65, 70, 75, 80, 85 or 90 or more years old.

In a most preferred embodiment of the invention, is provided a non-pathogenic non-viable *Mycobacterium* for use in the treatment, reduction, inhibition or control of cancer in a subject, wherein the subject is a human patient clinically classified as having a performance status of 1-, 2, 3 or 4 according to the Eastern Cooperative Oncology Group (ECOG) Scale, suitably PS 2, wherein the subject wherein the human patient is 70 or more years old, optionally wherein the human patient is administered gemcitabine, optionally in combination with nab-paclitaxel, preferably having a performance status of 2 (PS 2).

In a most preferred embodiment of the invention, is provided a non-pathogenic non-viable *Mycobacterium* for use in the treatment, reduction, inhibition or control of cancer in a subject, wherein the subject is clinically classified as having a performance status of 0, 1, 1-, 2, 2+, 3, 4, according to the ECOG Scale, suitably a PS between 0 and 2, wherein the subject is a human patient is 70 or more years old, optionally wherein the human patient is administered gemcitabine, optionally in combination with nab-paclitaxel.

Preferably, said human patient of 70 or more years old has a performance status of 0, 1, or 1-.

The invention is further described with reference to the following non-limiting Examples.

Example 1

A study has been developed to investigate the safety and efficacy of gemcitabine in combination with pembrolizumab and a preparation of heat-killed whole cell *M. obuense* (IMM-101) in patients clinically classified as having a performance status of 2 according to the ECOG Scale, or classified as not being sufficiently fit to tolerate two or more chemotherapy regimens, e.g. PS 1(–). The combination will be used as first line treatment for metastatic pancreatic cancer in patients with such lower performance status, using objective response rate (ORR) as the primary endpoint. The trial will also provide and/or determine: assessment of safety profile using CTCAE v5, assessment of ORR using iRECIST, assessment of duration of response, progression-free survival (PFS) and disease control rate (DCR) using RECIST1.1 and iRECIST, Overall survival (OS), and to correlate molecular profile and hypothesised biomarkers of therapy response generated from tumour and blood samples to ORR, PFS, OS and DCR.

The overall design uses two single arm phase II three-stage approaches, separately for PS1– and PS2 patients, which have good power (>87% for PS1–; >88% for PS2) to detect response rates of ≥30% and ≥20% in PS1– and PS2 patients respectively. Up to 40 PS1– patients and 40 PS2 patients are to be recruited.

The primary endpoint is ORR assessed by RECIST1.1. Response will be assessed by CT every 6 weeks; the minimum follow-up for patients prior to the planned futility/efficacy analyses will be 18 weeks (i.e. after the 3rd response assessment time) but in practice, most patients will have greater than 18 weeks follow-up at the time of interim analyses. All patients who start study treatment will be evaluable for response and form part of the denominator for calculating response rate. Secondary endpoints will be safety profile (using CTCAE v5), ORR assessed by iRE-CIST, duration of response (by RECIST1.1 and iRECIST), progression-free survival (PFS) assessed by RECIST1.1 and iRECIST, OS, DCR assessed by RECIST1.1 and iRECIST. Exploratory endpoints will include analysis of tumour and blood samples to determine molecular profile and biomarkers of therapeutic responsiveness with correlation to ORR, PFS, OS and DCR.

The patients will be dosed as follows: IMM-101: 1 mg intra-dermal (ID) Week 0, 2 and 4, then 0.5 mg ID Q3W from Week 8; Pembrolizumab: 200 mg IV Q3W from Week 2; Gemcitabine: 1000 mg/m2 IV on day 1 and day 8 every 21 days from Week 2.

The trial design protocol is depicted in FIG. 1.

Example 2

A further study has been developed to investigate the safety and efficacy of IMM-101 in combination with gemcitabine and nab-paclitaxel as a First Line Therapy in Patients with Metastatic Pancreatic Ductal Adenocarcinoma (mP-DAC) and an ECOG Performance Status of PS 2. This study is for patients recently diagnosed with mPDAC and who have not received any treatment yet for their cancer. Based on an assumed control median survival time of approximately 6 to 8 months, and an expected benefit of at least 50% in the intervention arm, a study with a total of 256 events (deaths) has 90% power to reject the null hypothesis of HR=1 at the 5% significance level (this size study also has reasonable power [77%] to detect a benefit of at least 40% in the intervention arm). Assuming that recruitment may take at least 12 months, and with a follow-up time of 2 years, 256 events are anticipated with approximately 320 randomized patients. 320 patients will be recruited.

To be eligible for entry into this study, patients must have an ECOG/WHO Performance Status of at Week 0, Visit 1 or over 70 years of age. All patients with a PS of 2 (no matter their age) or over 70 years (no matter their performance status) will be candidates for this study. ECOG PS will be conducted by 2 investigators at the site and in case of conflicting evaluations, the highest (worst) assessment will be used. Suitable patients are, in the opinion of the Investigator, considered non-eligible to receive FOLFIRINOX but eligible to receive Gem/Nab-P. Patients with any germline mutation (BRCA2, p16, ATM, STK11, PRSS1/PRSS2, SPINKI, PALB2 etc.) can be enrolled into the study at the investigator discretion.

Vitamin D levels will be measured in all patients at screening, patients with levels lower than the normal range will be supplemented in order to normalize their levels while receiving the investigational product. Patients are recruited according to adequate organ function, as defined by the following: a. Serum aspartate aminotransferase (AST) and serum alanine aminotransferase (ALT)<2.5× upper limit of normal (ULN) or, or in case of liver metastasis 5×ULN; b. Total serum bilirubin<1.5 ULN. Patients with a biliary stent may be included if bilirubin level after stent insertion decreased to 1.5×ULN and there is no cholangitis; c. Serum albumin 2.8 g/dL; d. Haemoglobin 9.0 g/dl; e. White blood cell count (WBC) 3,000/μL; f. Absolute neutrophil count (ANC) 1,500/μL; g. Platelets 100,000/μL, h. Serum creatinine 1.5 ULN or creatinine clearance>50 mL/min (MDRD).

Once consented and prior randomization, patients will undergo screening tests. Qualifying patients will be randomized in a 1:1 ratio to either Gem/Nab-P+IMM-101 or Gem/Nab-P only, with randomization stratified by geographical region (Europe vs. outside Europe), performance status (0 or 1 vs. 2) and age group (up to and including 70 years vs. older than 70 years).

At progression and removal from study, and at PI discretion, IMM-101 may be administered on a monthly base alone or in combination with other therapies until death or intolerable toxicity considered related to IMM-101.

Patients will be evaluated according to the schedule of events in order to determine their performance on investigational study medications. Various laboratory evaluations, imaging and quality of life questionnaire will be performed from the screening to the last follow-up study visit.

The primary objective is to evaluate the safety and tolerability of the combination of gemcitabine/nab-paclitaxel±IMM-101 in mPDAC patients by examining the profile of adverse events experienced (changes in clinical status and in laboratory parameters, including local tolerability at the injection site injection of IMM-101). A further primary objective is to improve Overall Survival (OS).

The co-primary objectives are: to evaluate the Progression-free Survival (PFS) at 12-month treatment in mPDAC. PFS will be evaluated using RECIST 1.1, and also iRECIST principles. It is also intended to evaluate Overall Survival (OS) at 12-month treatment.

The secondary objectives are: to evaluate the Duration of Response (DoR) and Time to Response (tTR) in mPDAC patients as assessed by RECIST 1.1 and iRECIST; to evaluate the Overall Response Rate (ORR) e.g. using immune-related Response Criteria (irRC); to assess the percentage of patients with objective response; to evaluate and assess percentage Disease Control (CR, PR, SD) following iRE-CIST principles. based on RECIST 1.1 (e.g. assessed at each scan assessment point); PFS assessed at 2 and 5-year; OS at 2 and 5-year; Quality of Life Questionnaires C30 (QLQ-C30) will be completed at the start, then after 4 weeks, 3, 6 and 12 months.

The exploratory objectives are: to evaluate the immunological changes evaluated at different times points on blood samples and, when possible, on biopsy samples. Endpoints may include a change in one or more markers of immune status based on cellular involvement, function or cytokine/immune mediator production such as, for example, cytokines and antibodies, or any other clinically or immunologically relevant assays that may become pertinent.

The patients will be doses as follows: IMM-101: A single 0.1 mL intradermal injection of IMM-101 (each vial contains 10 mg/mL); Gemzar (gemcitabine): (1000 mg/m$^2$ for i.v. infusion; Abraxane: Nab-paclitaxel 125 mg/m$^2$, i.v. infusion.

IMM-101 is given via intradermal injection into the skin overlying the deltoid muscle, with the arm being alternated between each dose.

IMM-101 Dosing Regimen: IMM-101 will always be administered first, 2 weeks before the administration of gemcitabine and nab-paclitaxel.

The treatment regimen with IMM-101 will be one dose given every 2 weeks for the first 3 doses followed by a rest period of 4 weeks, then one dose every 2 weeks for the next 3 doses. The initial IMM-101 dose administered is 0.1 mL. This is followed by a dose of 0.05 mL or 0.1 mL of IMM-101 every 4 weeks thereafter for up to 12 months or longer; the first IMM-101 dose administered 3 days before the first dose of gemcitabine.

Gemcitabine/nab-paclitaxel will be administered as follows: Nab-paclitaxel 125 mg/m$^2$, i.v. infusion over about 30 minutes followed by Gemcitabine 1000 mg/m$^2$ as a 30-minute i.v. infusion on D1, D8, D15 of a 28-day cycle.

Interim Safety Assessment: A formal early safety assessment will be performed when the first 30 patients in the IMM-101 arm have received 3 cycles of treatment (12 weeks). A data safety monitoring board (DSMB) will evaluate the data from patients in this phase which will ultimately be combined for analysis with all subsequently enrolled patients. A specific data safety monitoring charter (DSMC) will be created to describe all the modus operandi of the DSMB. If no exacerbated or unacceptable toxicity is observed in this cohort after 3 cycles/12 weeks, these patients and the subsequent patients recruited on study will be monitored based on unacceptable toxicity (dose limiting toxicity or DLT).

Interim analysis: In addition to the early safety assessment after 30 patients in the IMM-101 arm have received 3 cycles of treatment, a formal interim analysis for efficacy will be conducted when the 320th patient has been randomized. If the null hypothesis is not rejected, the study will continue unaltered, and the final analysis will be conducted when 256 deaths have occurred.

Example 3

This study is described in U.S. Pat. No. 8,617,520 assigned to the applicant, and the results were published by Dalgeish et al, in the paper entitled "Randomised, open-label, phase II study of gemcitabine with and without IMM-101 for advanced pancreatic cancer". [*Br. J. Cancer.* 2016 Sep. 27; 115(7): 789-796] and also as "Long term survival in IMAGE 1 (Immune Modulation And Gemcitabine Evaluation 1), a randomized, open-label phase II trial comparing gemcitabine with and without IMM-101 in advanced pancreatic cancer"; Angus George Dalgleish and The IMAGE 1 Trial Investigators; Journal of Clinical Oncology 2015 33:15_suppl, 3051-3051.

In summary, this study compared, in patients with advanced pancreatic cancer, the effects of gemcitabine (GEM) in combination with IMM-101 (a suspension of heat-killed whole cell *M. obuense* in borate-buffered saline) to gemcitabine alone on: Safety and tolerability, including QoL; clinical signs and symptoms of disease; Overall survival (OS), progression-free survival (PFS), and overall response rate (ORR; Selected markers of tumour burden and immunological status Disease outcome—patients, who provided informed consent, participated in a screening period of up to 28 days to establish eligibility. Once eligibility was confirmed, patients were randomised (2:1) to receive either: Chemotherapy (GEM) with IMM-101 (active group) or chemotherapy (GEM) alone (control group).

Randomisation was stratified by baseline World Health Organisation (WHO) performance status (PS 0-1 vs. PS 2) and extent of disease (locally advanced inoperable vs. metastatic [irrespective of primary tumour] vs. disseminated peritoneal disease vs. any combination of these). The patient then entered the Treatment Phase of the study.

The combination treatment regimen comprised administration of a single 0.1 ml intradermal injection of IMM-101 into the skin overlying the deltoid muscle, with the arm being alternated between each dose, every 2 weeks for the first 3 doses followed by a rest of 4 weeks then every 2 weeks for the next 3 doses followed by every 4 weeks thereafter, with chemotherapy beginning at least 14 days after first dose of IMM-101, wherein administration of gemcitabine was administered intravenously at 1000 mg/ml over 30 minutes once weekly for 3 consecutive weeks out of every 4 weeks, up to a maximum of 12 cycles (i.e. approximately 48 weeks). The active comparator arm received the normal standard of care—up to 12 cycles of gemcitabine. Dosing of gemcitabine was as per the normal prescribing information for pancreatic cancer.

In a pre-defined metastatic subgroup (84%), OS was significantly improved from 4.4 to 7.0 months in favour of IMM-101+GEM (HR, 0.54, 95% CI 0.33-0.87, P=0.01).

Thirteen patients with a WHO performance status of 2 were randomised to the IMM 101 treated group (total 75 patients; 17.3% PS2). In the IMM-101 treated group, six patients with PS2 were male and seven female. The age range was 45-75 years (median 66). Time on study ranged from 0.5 to 46.5 months—seven patients were on study for at least 6 months. The three PS2 patients in the Control group were aged 57, 67 and 83 years; one was male and two were female. Time on study was 1.9, 2.4 and 6.4 months. Two of the 13 patients in the IMM-101 treated group with WHO PS 2 completed the study (12 cycles of treatment) and enrolled in the IMM-101-002A Sub Study where they continued to receive IMM-101 (patients 1030 and 1043). One patient of PS2 in the IMM-101 treated group had a response (PR, following initial progression, patient 1030). Four patients had a BOR of SD, for a further 6 patients the BOR was PD and 2 patients were non-evaluable for response. In the Control group the BOR was PD for 2 patients and the third was non-evaluable Most notably, for patients in the IMM-101 treated group with a WHO performance status of 2, the median OS for the ITT analysis set was 7.5 months. This was higher than the median for the PS 0-1 subgroup (6.4 months). Nine of the thirteen patients survived for at least 7 months.

Example 4

A study has been developed to investigate the adjuvant effects of atezolizumab in combination with a preparation of heat-killed whole cell *M. obuense* (IMM-101) in patients with MSI-H/dMMR stage III colorectal cancer for whom oxaliplatin regiments are not a viable treatment option.

Patients to be treated have an ECOG status of 0-2, have undergone R0 tumor resection, and exhibit pathological stage III histologically-confirmed adenocarcinoma of the colon or rectum who are ineligible for, or in refusal of, oxaliplatin based adjuvant chemotherapy.

This study seeks to investigate whether the adjuvant combination of IMM-101 with atezolizumab is well-tolerated and to investigate efficacy signals of the combination, as well as determine whether the adjuvant combination of IMM-101 with atezolizumab can significantly improve disease-free survival rate at 3 years, as well as estimating the ctDNA-free rate defined as the proportion of patients without detectable ctDNA after 12 months of adjuvant treatment.

A total of 100 patients are enrolled, wherein 50 are in cohort A, and 50 are in cohort B. A sample size of N=50 is considered to provide a reasonably reliable estimate of the 3-year disease-free survival rate for the experimental combination treatments, allowing gauging of the actually observed rate against a prospectively enrolled cohort of patients with stage III dMMR tumors in the COLOPREDICT registry.

Cohort A receive atezolizumab, in an adjuvant setting, at a dose of 840 mg, administered intravenously, every 2 weeks for 12 months.

Cohort B receive, in an adjuvant setting, one initial dose of 1.0 mg IMM-101 administered intradermally at day 14±2 days before the start of atezolizumab treatment. Then, patients are administered atezolizumab at a dose of 840 mg, administered intravenously every 2 weeks for 12 months, in combination with IMM-101 at a dose of 0.5 mg intradermally, every 2 weeks for one month, and subsequently at a dose of 0.5 mg intradermally every 4 weeks for a total of 12 months.

The dose volume of IMM-101 is initially 0.1 mL (1.0 mg), followed by 0.05 mL (0.5 mg), administered intradermally into the skin overlying the deltoid muscle, with the arm being alternated between each dose. The Investigator will have been appropriately trained a priori in the technique of intradermal injection.

Figure 2:
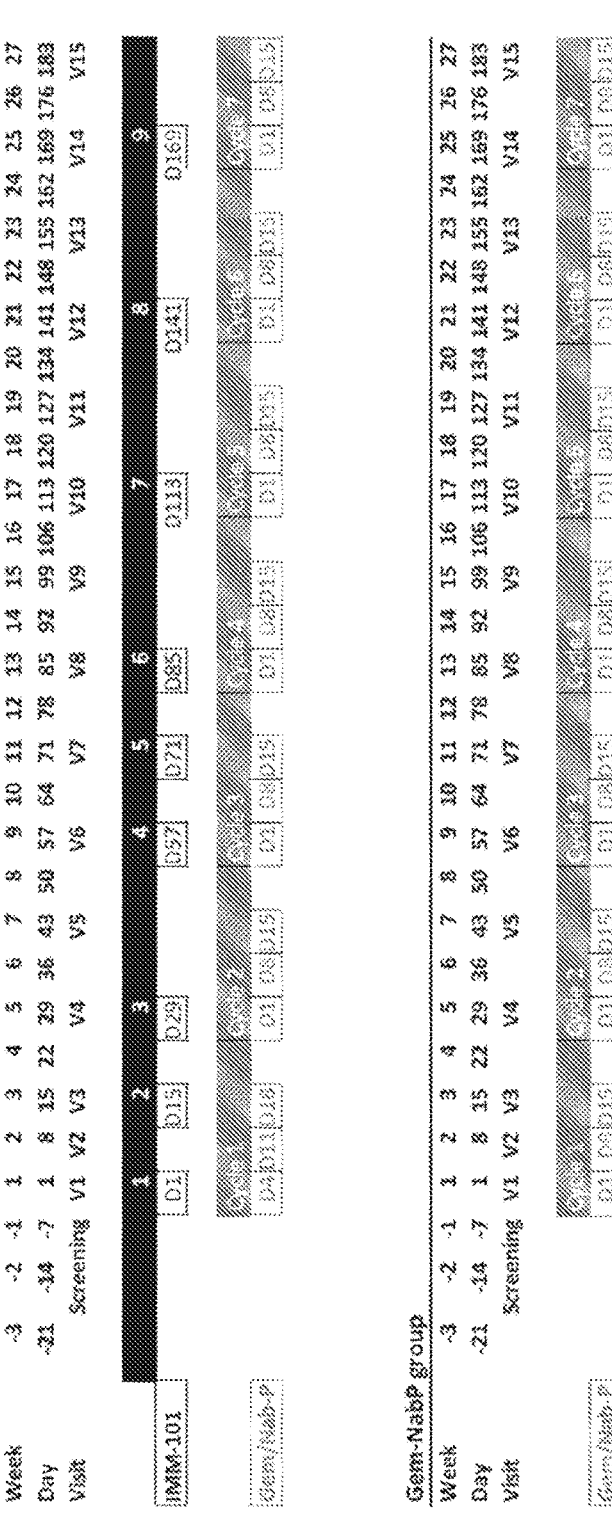
FIG. 2 shows a schematic of a clinical trial investigating the safety and efficacy of IMM-101 in combination with gemcitabine and nab-paclitaxel (Gem/Nab-P) as a first line therapy in poor performance status (PS) or elderly patients with metastatic pancreatic ductal adenocarcinoma (mPDAC), under Example 2.

Previous clinical experience with IMM-101 has suggested that this dose is safe and well tolerated. The skin reaction that develops at the site of injection is characterised by erythema, local swelling and occasionally mild ulceration. All symptoms are to be expected given the known pharmacology of the product and previous clinical experience. Furthermore, data from safety and tolerability studies with IMM-101 have revealed that skin reactions resolve satisfactorily over time and do not impair daily activity, The first dose of IMM-101 administered to each patient in the study is followed by vital signs monitoring for at least 2 hours under medical supervision with resuscitation facilities available as a precautionary measure. Patients are followed up for three years following the last dose of therapy where the primary endpoint is an assessment of the DFS rate at the 3-year milestone, with secondary endpoints to include DFS/OS at 1, 2 and 5 years, safety, QoL and rate of ctDNA free patients at 12 months following the end of therapy—see FIG. 2.

Patient inclusion criteria include: hemoglobin of at least 9 g/dL; AST (SGOT)/ALT (SGPT) value of 2.5, with endpoints to further include: death from any cause 3 years after randomization.

Example 5

An explorative sub-study to Example 4 has been developed to assess the efficacy of perioperative/peri-adjuvant atezolizumab with IMM-101 in patients with MSI-high/dMMR clinical stage III colorectal cancer for whom oxaliplatin regimens are not a viable treatment option in terms of pathological complete (pCR) or subtotal (<10% vital tumour cells) regression after 5 weeks treatment, and in terms of disease-free survival and overall survival.

A total of 20 patients are enrolled, wherein patients to be treated exhibit clinical stage III histologically-confirmed adenocarcinoma of the colon or rectum who are ineligible for, or in refusal of, oxaliplatin based adjuvant chemotherapy, an ECOG status of 0-2 and a present with a resectable primary tumor. After resection, these patients will receive the adjuvant therapy of Example 3, Cohort B, for an additional 12 months.

Specifically, enrolled patients receive atezolizumab at a dose of 1200 mg, administered intravenously, 28 days and 7 days prior to tumor resection surgery, in combination with IMM-101 at a dose of 1.0 mg, administered intradermally, 35 days prior to tumor resection surgery, followed by IMM-101 administered at a dose of 0.5 mg 21 days and 5 days prior to resection surgery.

Within 70 days after resection surgery, patients will receive one initial dose of 1.0 mg of IMM-101 administered intradermally at day 14±2 days before the start of atezolizumab treatment. This is followed by administration of atezolizumab at a dose of 840 mg, administered intravenously, every 2 weeks for 12 months, in combination with IMM-101 at a dose of 0.5 mg, every 2 weeks for one month, and subsequently every 4 weeks for a total of 12 months, as per the adjuvant setting of Example 4, Cohort B.

Figure 3:
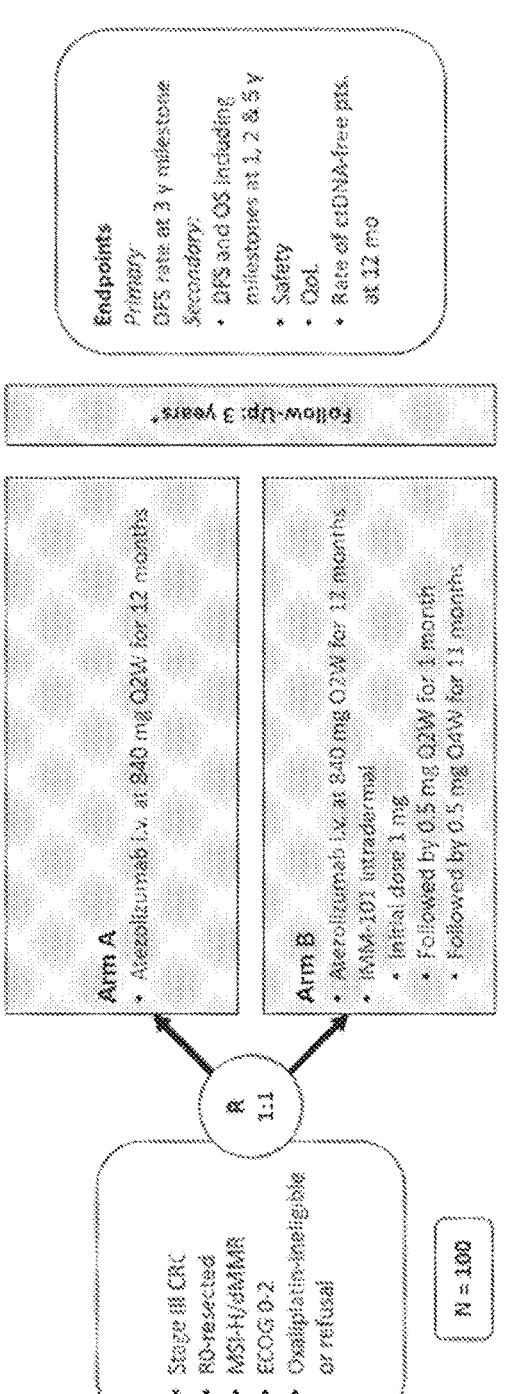
FIG. 3 shows a schematic of a clinical trial investigating the adjuvant (post-surgical) use of a combination according to the invention, specifically *M. obuense* with the checkpoint inhibitor (anti-PD-L1) atezolizumab, in the treatment of Stage III, R0 resected, MSI-high/dMMR patients, who are ineligible for oxaliplatin or refused said agent, and who present with an ECOG Performance Status of 0, 1 or 2 (see Example 4).
Figure 4:
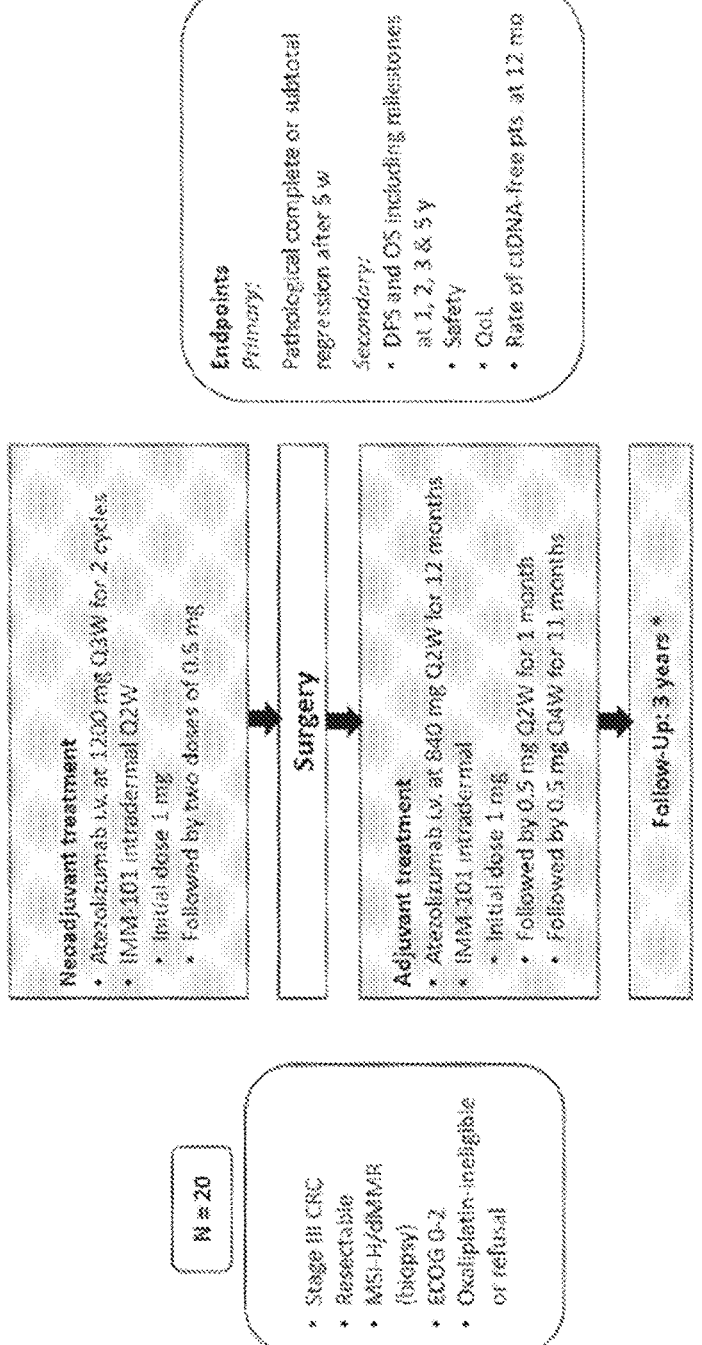
FIG. 4 shows a schematic/flow chart of a clinical trial investigating the neo-adjuvant (pre-surgical) use and adjuvant (post-surgical) use, together a peri-adjuvant regimen, of a combination according to the invention, specifically *M. obuense* with the checkpoint inhibition (anti-PD-L1) atezolizumab, in the treatment of Stage III, resectable MSI-high/dMMR patients, who are ineligible for oxaliplatin or refused said agent, and who present with an ECOG Performance Status of 0, 1 or 2 (see Example 5).

Patients are followed up for three years following the last dose of therapy where the primary endpoint is an assessment of the DFS rate at the 3-year milestone, with secondary endpoints to include DFS/OS at 1, 2 and 5 years, safety, QoL and rate of ctDNA free patients at 12 months following the end of therapy—see FIG. 3. Patient inclusion criteria include: hemoglobin of at least 9 g/dL; AST (SGOT)/ALT (SGPT) value of 2.5, with endpoints to further include: death from any cause 3 years after randomization.

The invention claimed is:

1. A method of treating, reducing, inhibiting or controlling cancer in a subject, wherein said subject is a human patient and wherein said method comprises simultaneously, separately or sequentially administering to the subject (i) one or more therapeutic agents and/or cancer treatments and (ii) a non-pathogenic non-viable *Mycobacterium*, wherein said method results in enhanced therapeutic efficacy relative to administration of one or more therapeutic agents and/or cancer treatments alone, wherein the human patient is clinically classified as having a performance status of 2, 3 or 4 according to the Eastern Cooperative Oncology Group (ECOG) Scale, wherein the human patient is classified as not being of an age and/or sufficiently fit to tolerate two or more chemotherapy regimens and, optionally, are considered eligible to receive gemcitabine and nab-paclitaxel.

2. The method according to claim 1, wherein said human patient is clinically classified as having a performance status of 2, 3 or 4 according to the ECOG Scale by at least two clinical observers, wherein in the event of conflicting evaluations, the highest (worst) assessment is used.

3. The method according to claim 1, wherein the non-pathogenic non-viable *Mycobacterium* is selected from *M. vaccae; M. obuense, M. parafortuitum, M. paratuberculosis, M. brumae, M. aurum, M. indicus pranii, M. manresensis, M. kyogaense, M. phlei, M. smegmatis, M. tuberculosis* Aoyama B, H37Rv, BCG, VPM1002BC, SMP-105, Z-100 and combinations thereof.

4. The method according to claim 1, wherein the non-pathogenic non-viable *Mycobacterium* is heat killed.

5. The method according to claim 1, wherein the non-pathogenic non-viable *Mycobacterium* is the rough variant and/or a presented as a fraction, fragment, sub-cellular component, lysate, homogenate, sonicate, or substantially in whole cell form.

6. The method according to claim 5, wherein the non-pathogenic non-viable *Mycobacterium* is administered to the human patient as a first line treatment simultaneously, separately or sequentially with the administration of one or more therapeutic agents or modalities that are selected from adoptive cell therapy, surgical therapy, chemotherapy, radiation therapy, hormonal therapy, checkpoint inhibitor therapy, small molecule therapy, receptor kinase inhibitor therapy, hyperthermia treatment, phototherapy, radiofrequency ablation therapy (RFA), anti-angiogenic therapy, cytokine therapy, cryotherapy, biological therapy, HDAC inhibitor therapy, BRAF inhibitor therapy, MEK inhibitor therapy, EGFR inhibitor therapy, VEGF inhibitor therapy, P13K delta inhibitor therapy, PARP inhibitor therapy, mTOR inhibitor therapy, hypomethylating agents, oncolytic virus, TLR agonists, STING agonists, mifamurtide, and cancer vaccines.

7. The method according to claim 6, wherein the human patient also receives one or more cytotoxic chemotherapeutic agents, optionally wherein the subject demonstrated a partial response or stable disease following FOLFIRINOX therapy.

8. The method according to claim 7, wherein the one or more cytotoxic chemotherapeutic agents comprise: a) gemcitabine; or b) nab-paclitaxel, optionally in combination with gemcitabine.

9. The method according to claim 1, wherein the human patient is also administered one or more checkpoint inhibitors.

10. The method according to claim 9, wherein the one or more checkpoint inhibitors is selected from ipilimumab, nivolumab, pembrolizumab, azetolizumab, BI 754091, bavituximab, bintrafusp alfa, dostarlimab, durvalumab, tremelimumab, spartalizumab, avelumab, sintilimab, toripalimab, prolgolimab, tislelizumab, camrelizumab, MGA012, MGD013, KN046, MGD019, enoblituzumab, MGD009, MGC018, MEDI0680, miptenalimab, nimotuzumab, PDR001, FAZ053, TSR022, MBG453, relatlimab, LAG525, IMP321, REGN2810, REGN3767, pexidartinib, LY3022855, FPA008, BLZ945, GDC0919, epacadostat, emactuzumab, FPA150, indoximid, BMS986205, CPI-444, MEDI9447, PBF509, FS118, lirilumab, Sym023, TSR-022, A2Ar inhibitors, NKG2A inhibitors, monalizumab, and combinations thereof, optionally administered in a sub-therapeutic amount and/or duration.

11. The method according to claim 9, wherein administration of said non-pathogenic non-viable Mycobacterium is prior to and/or after the administration of one or more checkpoint inhibitors.

12. The method according to claim 1, wherein the cancer is selected from bladder cancer, prostate cancer, liver cancer, renal cancer, lung cancer, breast cancer, colorectal cancer, colon cancer, rectal cancer, pancreatic cancer, brain cancer, hepatocellular cancer, lymphoma, leukaemia, gastric cancer, cervical cancer, ovarian cancer, thyroid cancer, melanoma, head and neck cancer, skin cancer, soft tissue sarcoma and/or osteosarcoma.

13. The method according to claim 12, wherein the cancer is pancreatic cancer selected from locally advanced pancreatic cancer with or without nodal lesions, resectable pancreatic cancer, borderline resectable pancreatic cancer, unresectable pancreatic cancer, checkpoint-refractory pancreatic cancer, chemotherapy-refractory pancreatic cancer, oligometastatic pancreatic cancer, pancreatic ductal adenocarcinoma (PDAC), and metastatic pancreatic ductal adenocarcinoma (mPDAC).

14. The method according to claim 1, wherein the non-pathogenic non-viable Mycobacterium is administered by intratumoral administration sequentially followed by intradermal administration.

15. The method according to claim 1, wherein:

a) the treatment, reduction, inhibition or control of said cancer results in a clinically relevant improvement in one or more markers of disease status and progression selected from one or more of the following: (i) overall survival; (ii) progression-free survival; (iii) disease free survival; (iv) overall response rate; (v) reduction in primary tumour size and/or metastatic disease; (vi) circulating levels of tumour antigens; (vii) nutritional status; (viii) pain control or analgesic use; (ix) CRP/albumin ratio; (x) improved Quality of Life; (xi) maintenance of lean body mass; (xii) reduced potential or incidence of cachexia; or (xiii) a reduction or elimination in ctDNA, as assessed following surgery and/or end of therapy and/or following administration of 1, 2, 3, 4, 5 or 6 or more doses of said non-pathogenic non-viable Mycobacterium;

b) the treatment, reduction, inhibition or control of said cancer, which comprises a primary tumour and/or non-target tumours, results in subtotal regression as demonstrated by less than 10% vital tumour cells present in tumour biopsy or resected primary tumour, stable disease (SD), a complete response (CR) or partial response (PR) of the primary tumour; and/or subtotal regression as demonstrated by less than 10% vital tumour cells present in tumour biopsy or resected metastatic tumour, stable disease (SD) or complete response (CR) of one or more non-target tumours, as assessed by Immune Related Response Criteria (irRC), iRECIST, or irRE-CIST, as assessed following surgery and/or end of therapy and/or following administration of 1, 2, 3, 4, 5 or 6 or more doses of said non-pathogenic non-viable Mycobacterium;

c) the treatment, reduction, inhibition or control of said cancer, which comprises a primary tumour and/or non-target tumours, results in prolonged progression free survival according to RECIST 1.1 or iRECIST; prolonged Duration of Response (DoR) according to RECIST 1.1 or iRECIST; or an accelerated Time to Response (TtR) according to RECIST 1.1 or iRECIST, as assessed following surgery and/or end of therapy and/or following administration of 1, 2, 3, 4, 5 or 6 or more doses of said non-pathogenic non-viable Mycobacterium; or d) the treatment, reduction, inhibition or control of said cancer, which comprises a primary tumour and/or non-target tumours, results in (1) reducing or inhibiting formation or establishment of metastases arising from a primary tumour or cancer to one or more other sites, locations or regions distinct from the primary tumour or cancer; (2) reducing or inhibiting growth or proliferation of a metastasis at one or more other sites, locations or regions distinct from the primary tumour or cancer after a metastasis has formed or has been established; (3) reducing or inhibiting formation or establishment of additional metastasis after the metastasis has been formed or established; (4) prolonged overall survival; (5) prolonged progression free survival; (6) disease stabilisation; (7) increased quality of life, and combinations thereof.

16. The method according to claim 1, wherein the subject is a human patient of at least 50 years old.

17. The method according to claim 16, wherein the human patient is 70 or more years old.

18. The method according to claim 3, wherein M. vaccae is the M. vaccae strain deposited under accession number NCTC 11659 and associated designations SRL172, SRP299, IMM-201, DAR-901, or the M. vaccae strain as deposited under ATCC 95051.

19. Method according to claim 3, wherein M. obuense is the strain of Mycobacterium obuense deposited under the Budapest Treaty under accession number NCTC 13365.

20. The method according to claim 15, wherein the nutritional status is weight, appetite, or serum albumin.

* * * * *